(12) United States Patent
MacEwan et al.

(10) Patent No.: US 10,441,403 B1
(45) Date of Patent: Oct. 15, 2019

(54) BIOMEDICAL PATCH AND DELIVERY SYSTEM

(71) Applicant: Acera Surgical, Inc., St. Louis, MO (US)

(72) Inventors: Matthew R. MacEwan, St. Louis, MO (US); Ralph Dacey, St. Louis, MO (US); Wilson Z. Ray, St. Louis, MO (US)

(73) Assignee: Acera Surgical, Inc., St. Louis, MO (US)

( * ) Notice: Subject to any disclaimer, the term of this patent is extended or adjusted under 35 U.S.C. 154(b) by 36 days.

(21) Appl. No.: 14/213,216

(22) Filed: Mar. 14, 2014

Related U.S. Application Data

(60) Provisional application No. 61/798,224, filed on Mar. 15, 2013.

(51) Int. Cl.
*A61F 2/00* (2006.01)
*A61L 27/58* (2006.01)

(52) U.S. Cl.
CPC ............ *A61F 2/0063* (2013.01); *A61L 27/58* (2013.01); *A61F 2002/0072* (2013.01)

(58) Field of Classification Search
CPC ............ A61F 2/0063; A61F 2002/0072; A61F 27/58; A61F 2002/0068
USPC ................ 623/23.72; 606/151; 206/440–441
See application file for complete search history.

(56) References Cited

U.S. PATENT DOCUMENTS

| | | | |
|---|---|---|---|
| 3,280,229 A | 10/1966 | Simons | |
| 6,180,848 B1 * | 1/2001 | Flament | A61B 17/0057 606/151 |
| 2002/0173213 A1 * | 11/2002 | Chu | A61K 9/0024 442/414 |
| 2003/0004579 A1 * | 1/2003 | Rousseau | A61F 2/0063 623/23.72 |
| 2005/0104258 A1 | 5/2005 | Lennhoff | |
| 2005/0167311 A1 * | 8/2005 | Tonsfeldt | B65D 83/08 206/449 |
| 2005/0222591 A1 * | 10/2005 | Gingras | A61F 2/0063 606/151 |

(Continued)

FOREIGN PATENT DOCUMENTS

| | | |
|---|---|---|
| WO | WO 01/27365 | 4/2001 |
| WO | WO 2004/016839 | 2/2004 |

(Continued)

OTHER PUBLICATIONS

Park, S. et al., Apparatus for Preparing Electrospun Nanofibers: Designing and Electrospinning process for Nanofiber Fabrication, Polymer International, 2007, pp. 1361-1366.

*Primary Examiner* — Martin T Ton
(74) *Attorney, Agent, or Firm* — Knobbe, Martens, Olson & Bear, LLP

(57) ABSTRACT

A multi-laminar repair matrix for repairing a tissue defect may comprise a top patch and a bottom compliant patch. The bottom compliant patch may be compressed and sized to fit through a tissue defect, and expand to a substantially planar state after being implanted to the tissue defect. The top and/or bottom patch may include adhesives. A tool for implanting a patch to a tissue defect may include a shaft, a plurality of arms pivotally connected to the shaft, and a control. The control may be configured to radially expand the plurality of arms upon actuation of the control.

20 Claims, 19 Drawing Sheets

(56) References Cited

U.S. PATENT DOCUMENTS

| | | | |
|---|---|---|---|
| 2006/0264140 A1 | 11/2006 | Andrady | |
| 2007/0073344 A1* | 3/2007 | Jahns | A61B 17/0482 |
| | | | 606/232 |
| 2009/0228021 A1* | 9/2009 | Leung | A61B 17/06166 |
| | | | 606/139 |
| 2010/0092687 A1 | 4/2010 | Sumida et al. | |
| 2010/0185219 A1* | 7/2010 | Gertzman | A61L 31/005 |
| | | | 606/151 |
| 2011/0152897 A1* | 6/2011 | Bates | A61B 17/00234 |
| | | | 606/151 |
| 2012/0310260 A1* | 12/2012 | Hamlin | A61F 2/0063 |
| | | | 606/151 |
| 2013/0035704 A1* | 2/2013 | Dudai | A61F 2/0063 |
| | | | 606/151 |

FOREIGN PATENT DOCUMENTS

| | | |
|---|---|---|
| WO | WO 2006/096791 | 9/2006 |
| WO | WO 2006/123858 | 11/2006 |
| WO | WO 2007/086910 | 8/2007 |
| WO | WO 2011/095141 | 8/2011 |

* cited by examiner

BIOMEDICAL PATCH AND DELIVERY SYSTEM

PRIORITY CLAIM AND INCORPORATION BY REFERENCE

This application claims priority from U.S. provisional patent application No. 61/798,224 filed Mar. 15, 2013, which is hereby incorporated by reference in its entirety. Further, Patent Cooperation Treaty patent application number PCT/US2011/040691, filed Jun. 16, 2011 and titled "BIOMEDICAL PATCHES WITH ALIGNED FIBERS," and claiming priority to U.S. provisional patent application No. 61/355,712 filed Jun. 17, 2010, are both hereby incorporated by reference herein in their entirety.

BACKGROUND

The embodiments disclosed herein are directed to biomedical patches for repairing tissue defects, such as dural defects, and delivery systems applicable to same.

The human brain and spinal cord are surrounded by a system of three protective membranes known as the meninges: the pia mater, the arachnoid mater, and the dura mater. The meninges serve to maintain a layer of cerebrospinal fluid around the brain and spinal cord, protect the brain and spinal cord from trauma/abrasion, and support extra-cortical vasculature carrying blood to/from the brain. The dura mater is a thick fibrous membrane lining the inner surface of the skull and spinal column which forms a water-tight sac around the central nervous system and serves as the primary barrier between nervous tissue and the underlying bone. Given the critical role of the dura mater in maintaining a closed layer of cerebrospinal fluid around the brain and spinal cord, and in protecting cortical tissue from physical damage/irritation, the health, patency, and structure of the dura mater is essential to proper cortical functions.

The dura mater may sustain insults, injuries, or defects by accident, trauma, disease, or through routine surgical procedures. During the course of standard neurosurgical procedures the dura mater is commonly incised, resected, removed, or disrupted and must be repaired intraoperatively. In a large percentage of neurosurgical procedures surgeons must access anatomical sites within the skull, brain, spinal cord, and spinal column requiring disruption of the native dura mater. In the case of minimally invasive neurosurgical procedures (e.g. burr hole, shunt placement, ablation, etc.), the dura mater may only be minimally incised (defect <1 $cm^2$) to pass small tools into the underlying nervous tissue. In the case of more invasive neurosurgical procedures (e.g. decompressive craniotomy, tumor excision, trauma, etc.), the dura mater may be vastly resected or completely removed (defects >1000-1500 $cm^2$) to allow for cortical decompression or removal of diseased tissues. In all cases, regardless of the size or location of the dural defect, the dura mater must be repaired intraopertatively in order to restore the protective covering of the brain and reestablish the continuous layer of cerebrospinal fluid around the central nervous system. To facilitate this repair surgeons employ a type of surgical membrane or patch known as a "dural substitute."

Dural substitutes may comprise any type of material utilized to repair or replace the dura mater and promote healing and/or regeneration of native dura, a process known as "neoduralization". In all instances dural substitutes must cover the dural defect, enable a water-tight seal of dural defect, and provide a suitable scaffold for the ingrowth of native dural fibroblasts. As a result the majority of dural substitutes comprise a planar material which may be sutured into the native dura or passively draped over the dural defect to close the dural defect.

SUMMARY

In some embodiments, a repair matrix for repairing a tissue defect may comprise a compliant patch, wherein the compliant patch is configured to be compressed and sized to fit through the tissue defect when in a first state, and the compliant patch is configured to be substantially planar when in a second state. The compliant patch may comprise a first adhesive, the compliant patch may define an outer surface when in the first state, and the first adhesive may be located on the outer surface. The compliant patch may comprise electro-spun fibers. The compliant patch when in the second state may have a shape that follows a perimeter of the tissue defect. The shape of the compliant patch when in the second state may be square, rectangular, circular, triangular, elliptical, hexagonal, or quadrilateral. The compliant patch may be configured to biodegrade after being implanted to the tissue defect. In some embodiments, the tissue defect is a dural defect.

In some embodiments, the repair matrix for repairing a tissue defect may further comprise a second patch. The second patch may be complaint. The second patch may comprise a second adhesive. The second patch may comprise electro-spun nanofibers. The shape of the second patch may follow a perimeter of the tissue defect. The shape of the second patch may be square, rectangular, circular, triangular, elliptical, hexagonal, or quadrilateral. The second patch may be configured to biodegrade after being implanted to the tissue defect.

In some embodiments, a central region of the compliant patch may be adhered to a central region of the second patch via an adhesive. In some embodiments, the compliant patch and the second patch may be separated by a third layer disposed in between the compliant patch and the second patch, wherein the compliant patch is in the second state. The third layer may comprise an adhesive. The third layer may comprise the same material as the material of the compliant patch and/or the second patch. The size of the third layer may be smaller than the size of the compliant patch, and the size of the third layer may be smaller than a size of the second patch, thereby leaving a slot around a peripheral region of the compliant patch and the second patch.

In some embodiments, a kit for repairing a tissue defect may comprise a sterile easily opened packet containing a plurality of patches configured to repair a tissue defect, wherein each patch is progressively larger and the plurality of patches has same shape, wherein a number and sizes of the patches are such that at least one of the plurality of patches is correctly sized to repair a particular known type of tissue defect for a range of expected patients. The shape of the patches may be square, rectangular, circular, triangular, elliptical, hexagonal, or quadrilateral.

In some embodiments, a tool for repairing a tissue defect may comprise a shaft; a plurality of arms pivotally connected to a distal end of the shaft; and a control operably connected to the plurality of arms, wherein the control is configured to radially expand the plurality of arms upon actuation of the control. The plurality of arms may be biased radially. The plurality of arms may be configured to receive a compliant patch in a compressed state, wherein the plurality of arms is configured to expand a compliant patch loaded onto the plurality of arms from the compressed state to a substantially planar state upon radial expansion of the plurality of arms. The compliant patch in the compressed state may be sized to fit through the tissue defect. The complaint patch when in the substantially planar state may have a square, rectangular, circular, triangular, elliptical, hexagonal, or quadrilateral shape.

In some embodiments, a tool for repairing a tissue defect may comprise a proximal shaft, wherein a distal end of the proximal shaft is configured to removably connect to a proximal end of a distal shaft that is pivotally connected to a plurality of arms, wherein the proximal shaft comprises a control configured to operably connect to the plurality of arms via the distal shaft, wherein the control is configured to radially expand the plurality of arms upon actuation of the control. The tool may further comprise a cartridge for use with the tool, wherein the cartridge comprises the distal shaft and a compliant patch in a compressed state loaded onto the plurality of arms pivotally connected to the distal shaft, wherein the plurality of arms is configured to expand the compliant patch from the compressed state to a substantially planar state upon radial expansion of the plurality of arms. The compliant patch when in the substantially planar state may have a square, rectangular, circular, triangular, elliptical, hexagonal, or quadrilateral shape.

In some embodiments, a kit for repairing a tissue defect may comprise a patch delivery system. The patch delivery system may comprise a shaft, a plurality of arms pivotally connected to a distal end of the shaft, and a control operably connected to the plurality of arms, wherein the control is configured to radially expand the plurality of arms upon actuation of the control. The plurality of arms may be biased radially. The tissue defect may be a dural defect. The kit may further comprise a patch having a square, rectangular, circular, triangular, elliptical, hexagonal, or quadrilateral shape. The kit may further comprise a compliant patch in a compressed state loaded onto the plurality of arms, wherein the plurality of arms is configured to expand the compliant patch from the compressed state to a substantially planar state upon radial expansion of the plurality of arms. The compliant patch in the compressed state may be sized to fit through the tissue defect. The complaint patch when in the substantially planar state may have a square, rectangular, circular, triangular, elliptical, hexagonal, or quadrilateral shape.

In some embodiments, a kit for repairing a tissue defect may comprise a patch delivery system. The patch delivery system may comprise a proximal shaft, wherein a distal end of the proximal shaft is configured to removably connect to a proximal end of a distal shaft that is pivotally connected to a plurality of arms, wherein the proximal shaft comprises a control configured to operably connect to the plurality of arms via the distal shaft, wherein the control is configured to radially expand the plurality of arms upon actuation of the control. The kit may further comprise saline solution, sutures, gauze, a ruler, or any combination thereof. The kit may further comprise a patch having a square, rectangular, circular, triangular, elliptical, hexagonal, or quadrilateral shape. The kit may further comprise a cartridge for use with the patch delivery system. The cartridge may comprise the distal shaft and a compliant patch in a compressed state loaded onto the plurality of arms pivotally connected to the distal shaft, wherein the plurality of arms is configured to expand the compliant patch from the compressed state to a substantially planar state upon radial expansion of the plurality of arms. The kit may further comprise the distal shaft. The kit may further comprise a compliant patch in a compressed state loaded onto the plurality of arms pivotally connected to the distal shaft, wherein the plurality of arms is configured to expand the compliant patch from the compressed state to a substantially planar state upon radial expansion of the plurality of arms. The compliant patch when in the substantially planar state may have a square, rectangular, circular, triangular, elliptical, hexagonal, or quadrilateral shape.

DESCRIPTION

Multiple types of synthetic dural substitutes are available for use in repairing dural defects created during routine neurosurgical procedures. Yet, despite the present availability of dural substitutes, a substantial need exists for new dural substitutes that are easier to handle, increasingly reliable and suturable, increasingly compliant, faster to implant, effectively seal leaks in the dura, promote improved patient outcomes, and eliminate injurious side effects and complications.

Currently, defects in the dura mater are repaired by implanting a patch to the outer surface of the dura mater. The patch must be sutured or otherwise fixed to the tissue in order to prevent leaks of fluid such as cerebrospinal fluid (CSF) and migration of the patch. In addition, extra care must be taken for defects near the base of the skull where internal pressure is higher and leaks are more likely.

While the embodiments disclosed herein are described with reference to the dura mater and dural defects, they may be used with any suitable biological tissue and tissue defects. For example, the embodiments disclosed herein may be used in neosurgery, reconstructive surgery, plastic surgery, general surgery, minimally invasive surgery, orthopedic surgery, gastroenterology, wound care, and the like. Further, as used herein, the term "patch" may include a dural substitute, graft, mesh, membrane, scaffold, matrix, substrate, or replacement for any suitable biological tissue.

Because fluid inside the dura mater exerts an outward force, leaks would be more effectively prevented by implanting a patch to the inner surface of the dura mater. The need to suture and/or the small size of a dural defect, however, currently make it impractical to implant a patch to the inner surface.

Accordingly, the embodiments disclosed herein provide systems and methods for repairing a defect in a tissue, such as a dural defect, by implanting a patch to the inner surface of the tissue. In addition, a second patch may be implanted to the outer surface of the tissue defect. Adhesives may be included on the patch according to some embodiments of the invention in order to secure the patch to the tissue. The patch with adhesives may be used to repair a tissue defect from the outer surface, inner surface, or both. In addition, the shape of the patch and/or adhesives may be customized to repair the particular tissue defect being repaired. The embodiments disclosed herein further provide a system for delivering a patch to a tissue defect and encouraging effective cellular ingrowth and repair of a tissue defect.

Figure 1:
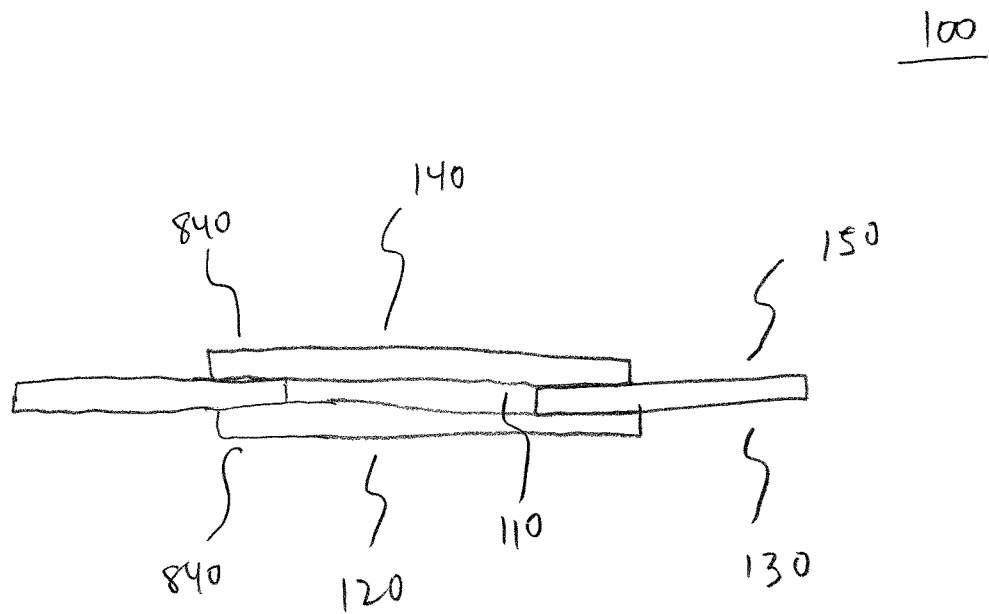
FIG. 1 illustrates a multi-laminar repair matrix applied to a tissue defect according to one embodiment.

FIG. 1 illustrates a side cross-sectional view of a multi-laminar repair matrix 100 according to some embodiments of the invention. FIG. 1 illustrates a top patch 140 and a bottom patch 120 implanted over a tissue defect 110, such as a dural defect. Referring to FIG. 1, the top patch 140 is applied to the outer surface 150 of the tissue defect 110, thereby patching the tissue defect 110. Still referring to FIG. 1, the bottom patch 120 is applied to the inner surface 130 of the tissue defect 130, thereby plugging the tissue defect 110. Some embodiments may comprise one or more layers of patches, both beneath and above the tissue defect 110. Referring to FIG. 1, patches 120, 140 may be larger than the tissue defect 110 such that the peripheral regions 840 of the patches 120, 140 contact the tissue surrounding the defect 110. Such a configuration may promote optimal closure of the defect 110 from all sides and approximate the surrounding tissue.

The materials, mechanical properties, and/or biological properties of the top patch 140 may be different from the bottom patch 120. In other embodiments, the materials, mechanical properties, and/or biological properties of the top patch 140 may the same as the bottom patch 120. The material of the patches 120, 140 may be polymeric or biologic optimized to promote cellular adhesion and/or tissue ingrowth.

In addition, the size, shape and/or geometry of the top patch 140 may be different from the bottom patch 120. In other embodiments, the size, shape and/or geometry of the top patch 140 may be the same as the bottom patch 120. In some embodiments, the bottom patch 120 may be smaller than the top patch 120. The small size of the bottom patch 120 may allow the bottom patch 120 to be inserted through the tissue defect 110. With the larger size of the top patch 140, a larger portion of the patch 140 may contact the tissue, thus promoting cellular ingrowth and sealing of the tissue defect 110. In addition, in order to prevent foreign body response, inflammatory response, and/or allergic response, the size of the top patch 140 may be limited. For example, the patch 120, 140 may extend over the tissue defect 110 such that there is sufficient contact between the tissue and the patch 120, 140 to promote cellular ingrowth and sealing of the tissue defect 110, without causing a foreign body response, an inflammatory response, and/or an allergic response. Thus, in some embodiments, the size of the top patch 140 may be optimized to promote cellular ingrowth and sealing while preventing foreign body response, inflammatory response, and/or allergic response. In some embodiments, the general shape of the top 140 and bottom 120 patches may be the same, although the patches 120, 140 may be different in size.

Further, the thickness of the top patch 140 may be different from the bottom patch 120. In other embodiments, the thickness of the top patch 140 may be the same as the bottom patch 120. In some embodiments, the thickness of the bottom patch 120 may be thinner than the top patch 140. The thinness of the bottom patch 120 may allow for greater flexibility and compliancy, so that the bottom patch 120 may be compressed and inserted through a tissue defect 110. The thickness of the top patch 140 may be thicker than the bottom patch 120, so that strength may be added to the multi-laminar repair matrix 100. In some embodiments, the thickness of the patch 120, 140 is between about 0.1 mm and 4 mm. In some embodiments, the side of the patch 120, 140 in contact with the tissue and directly proximate to the tissue defect 110 may promote cellular adhesion and/or tissue ingrowth. Thus, cellular ingrowth may occur in the tissue defect 110. In addition, the other side of the patch 120, 140 facing away from the tissue may prevent cellular adhesion and/or tissue ingrowth. Otherwise, cellular adhesion and/or tissue ingrowth on the side of the patch 120, 140 facing away from the tissue defect 110 may disadvantageously cause the patch 120, 140 to grow into the tissue.

Figure 2A:
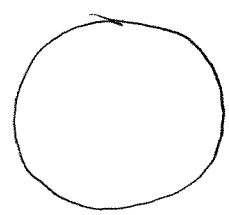
FIG. 2a illustrates a top view of one embodiment of a patch.
Figure 2B:
FIG. 2b illustrates a perspective view of one embodiment of a patch.
Figure 3:
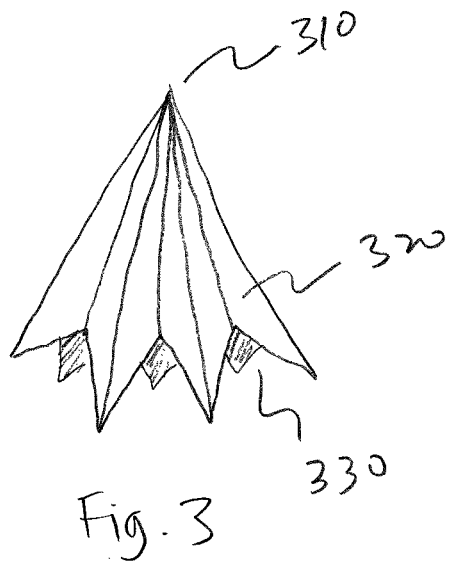
FIG. 3 illustrates a compressed patch according to one embodiment.
Figure 4:
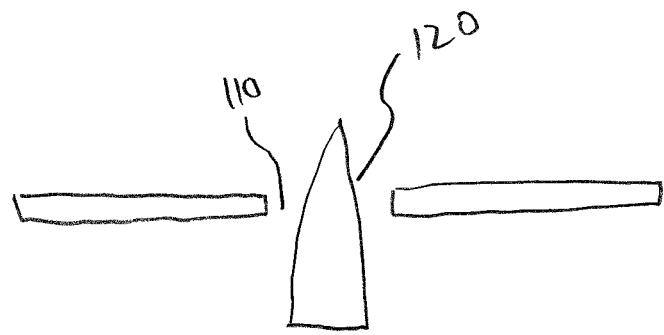
FIG. 4 illustrates a method of implanting a patch to a tissue defect according to one embodiment.
Figure 5:
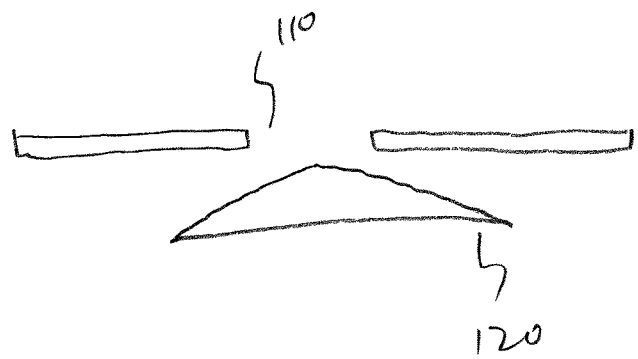
FIG. 5 illustrates a method of implanting a patch to a tissue defect according to one embodiment.
Figure 6:
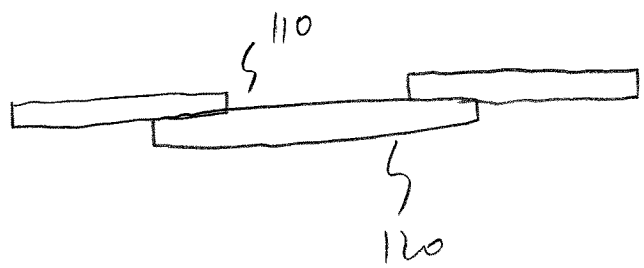
FIG. 6 illustrates a method of implanting a patch to a tissue defect according to one embodiment.
Figure 7:
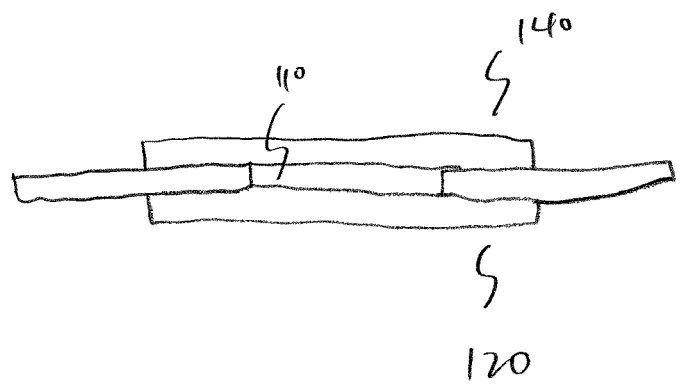
FIG. 7 illustrates a method of implanting a patch to a tissue defect according to one embodiment.

FIG. 2a illustrates a top view of a patch 120 in a planar state and FIG. 2b illustrates a perspective view of a patch 120 in a planar state. While FIGS. 2a-2b illustrate a circular patch 120, the patch 120 can be any shape, as further described herein. FIG. 3 illustrates a patch 120 in a compressed state. As illustrated in FIG. 3, in some embodiments, the patch 120 in a compressed state can resemble the canopy of a closed umbrella. FIGS. 4-6 illustrate a method of implanting a bottom patch 120 to the inner surface 130 of a tissue defect 110. In some embodiments, a method of implanting a bottom patch 120 to the inner surface 130 of a tissue defect 110 includes compressing the patch 120 from a planar state to a compressed state. In some embodiments, a patch 120 is pre-packaged in a compressed state. Referring to FIG. 4, the compressed patch 120 is then inserted through a tissue defect 110. In some embodiments, the bottom patch 120 may be implanted without drastic compression of the patch 120. For example, the tissue defect 110 may be sized such that a bottom patch 120 can be inserted through the tissue defect 110 without drastic compression of the patch 120. Referring to FIGS. 5-6, once the patch 120 is below the tissue defect 110, it is expanded to a substantially planar state. The patch 122 may be positioned as necessary so that it completely covers the tissue defect 110. Further, the patch 120 may be positioned to be flush against the tissue surrounding the defect 110, promoting intimate contact and repair of the tissue defect 110. Referring to FIG. 7, in some embodiments, a top patch 140 may also be implanted to the outer surface of the tissue defect 110. Further, in some embodiments, adhesives may be included on the top and/or bottom patch 120, 140 to secure the patches 120, 140 to the tissue defect 110 or to secure the patches 120, 140 to each other. The bottom patch 120 and/or top patch 140 may be implanted using a patch delivery system, which is further described herein.

In some embodiments, the bottom patch 122 is compliant so that it may be compressed and sized to fit through a tissue defect 110. In addition, a bottom patch 120 that is compliant can conform to the curvature of the tissue surrounding the defect 110, thereby forming a complete seal and minimizing the possibility of leaks. In some embodiments, a patch 120, 140 may become more complaint and flexible when hydrated. A compliant patch may comprise a dural substitute formed by electro-spinning methods, as described in PCT/US2011/040691, the entirety of which is hereby incorporated herein by reference. Accordingly, in some embodiments, the patches 120, 140 described herein may comprise electro-spun fibers. The fibers may comprise nanofibers, microfibers, or a combination of both. In some embodiments, the thickness of the patch 120, 140 is between about 0.1 mm and 4 mm.

Adhesives or adhesive properties may be included on or in the top patch 140 and/or bottom patch 120 for adhering the patch to a tissue or another patch and aid in patching and/or plugging a tissue defect 110. In some embodiments, the adhesives can be separate components from the patch 120, 140. In other embodiments, the adhesive property can be engineered into the material comprising the patch 120, 140. In some embodiments, the adhesive property can be integrally formed with the patch 120, 140. In some embodiments, the patch 120, 140 may comprise nano-fibers with electro static properties, thus exhibiting adhesive properties. In addition, the patch 120, 140 may exhibit adhesive properties in any number of additional ways. For example, the patch 120, 140 may be specially treated such that the patch exhibits adhesive properties. As used herein, it will be appreciated that references to adhesives may include any combination of the above.

The adhesives may be included on a patch 120, 140 in any number of different configurations or manners. For example, a patch 120, 140 may include any shaped adhesive, continuous adhesives, or discrete adhesives. In addition, adhesives may be included on the bottom patch 120 only, the top patch 140 only, and/or both the top 140 and bottom patch 120. The adhesive may be deposited onto a patch 120, 140 (or integrated onto the patch 120, 140, engineering into the patch 120, 140, etc.) in any number of ways, such as mask deposition, spray adhesive, stamping, coating, etc. In some embodiments, neither the top patch 140 nor bottom patch 120 includes adhesives.

In some embodiments, one side of a patch 120, 140 is wholly coated with adhesive (or adhesive is integrated onto the patch 120, 140, engineering into the patch, etc). In some embodiments, coating a patch 120, 140 with adhesive does not change the porosity of the patch 120, 140. For example, a patch 120, 140 may comprise a series of interconnected fibers, with pores or spaces between the connection points of the fibers. The patch 120, 140 may be coated with adhesive such that the adhesive coats the fibers, while leaving undisturbed the pores or spaces in the patch 120, 140. Accordingly, the adhesive does not detract from the rate and quality of cell ingrowth in the pores or spaces. In addition, in some embodiments, the adhesive does not detract from other properties of the patch 120, 140, such as mechanical properties, biocompatibility, handing, ease of use, implantation, and intraoperative delivery.

The adhesive can comprise more than 90%, 80%, 70%, 60%, 50%, 40%, 30%, 20%, 10%, or less of the patch area. According to some embodiments, the amount of adhesive covering a patch 120, 140 does not affect the compliancy of the patch 120, 140. In addition, in some embodiments, the amount of adhesive does not affect the flexibility, handling, and feel of the patch 120, 140 in some embodiments. In some embodiments, the compliancy of the patch 120, 140 is insignificantly reduced by the amount of adhesive.

Figure 8:
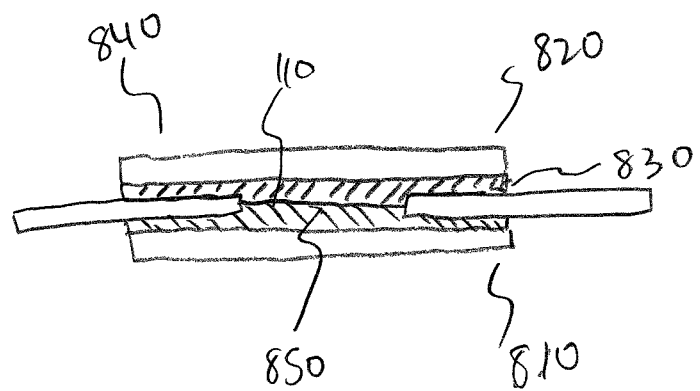
FIG. 8 illustrates an example of a multi-laminar repair matrix with adhesives according to one embodiment.
Figure 9:
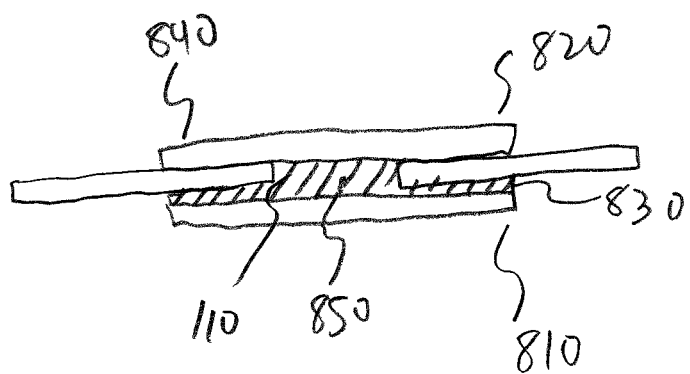
FIG. 9 illustrates an example of a multi-laminar repair matrix with adhesives according to one embodiment.

FIGS. 8-9 illustrate side views of a first patch 810 and a second patch 820 with exemplary configurations of adhesives 830. It will be appreciated that "first patch" and "second patch" are used for convenience to refer to a multi-laminar repair matrix 100 comprising a top patch 140 applied to the outer surface of a tissue defect 110 and a bottom patch 120 applied to the inner surface of the tissue defect 110, and that "first" or "second" does not necessarily refer to the top patch 140 or bottom patch 120. Thus, "first" may refer to a top patch 140 and "second" may refer to a bottom patch 120, or "first" may refer to a bottom patch 120 and "second" may refer to a top patch 140.

Referring to FIG. 8, two patches 810, 820 may be wholly covered with adhesive 830. Thus, when implanted, the peripheral regions 840 of the patches 810, 820 may adhere to the tissue surrounding the defect 110. Further, the adhesive 830 at the central region 850 of the first patch 810 may adhere through the tissue defect 110 to the adhesive 830 at the central region 850 of the second patch 820.

Referring to FIG. 9, the first patch 810 is covered by adhesive 830 and the second patch 820 does not include any adhesives 830 according to some embodiments of the invention. The patches 810, 820 may be implanted so that the peripheral region 840 of the first patch 810 adheres to tissue and adhesive 830 at the central region 850 of the first patch 810 adheres through a tissue defect 110 to the central region 850 of the second patch 820.

The adhesive 830 can promote faster healing time, improve quality repair of the tissue defect 110, and improve patient outcomes. Adhesive 830 between the tissue and patch 120, 140 can enhance the apposition and adhesion of the patch 120, 140 to the tissue, increase the strength of the seal, facilitate a water-tight seal, and encourage tissue ingrowth into the patch 120, 140 by promoting intimate contact with the tissue and cell sources/populations. Further, reinforcing tissue leads to lower risk of leaks. Similarly, adhesive 830 securing a top patch 140 and a bottom patch 120 to each other over a tissue defect 110 can promote secure closure of the tissue defect 110, a complete seal of the peripheral tissue, and cellular infiltration leading to regeneration of native tissue. Additionally, adhesives 830 securing a patch 120, 140 to a tissue, or adhesives 830 securing a patch 120, 140 to another patch 120, 140 through a tissue defect 110, may prevent migration of the patch 120, 140 and dehiscence and improve rates of defect sealing and wound healing.

Although FIGS. 8-9 illustrate adhesives on a multi-laminar system 100, adhesives may be used with a single-laminar system as well. In addition, in some embodiments, a multi-laminar system 100 does not include any adhesives.

Figure 10:
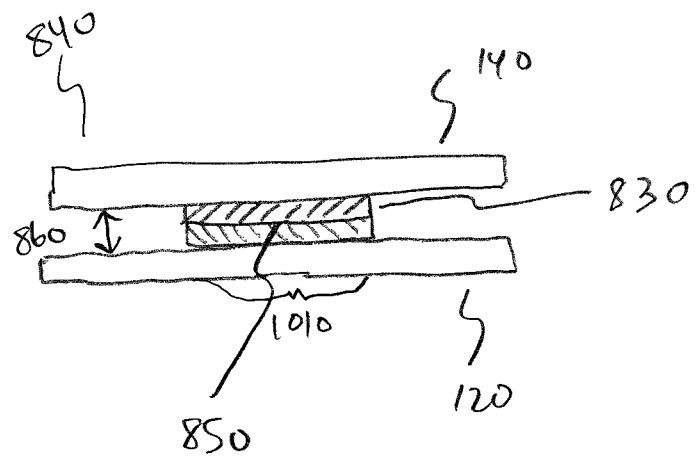
FIG. 10 illustrates two patches adhered together according to one embodiment.

Referring to FIG. 10, in some embodiments, two patches 120, 140 can be adhered to each other pre-operatively. For example, a central region 850 of the two patches 120, 140 can be adhered to each other, and the peripheral regions 840 of the patches 120, 140 may be free of adhesives 830. In some embodiments, the central region 850 of both patches 120, 140 may include adhesives 830 to adhere to each other, as illustrated in FIG. 10. In other embodiments, the central region 850 of only one patch 120, 140 may include adhesive, to adhere to the central region 850 of the other patch 120, 140. In some embodiments, the patches 120, 140 may have a radius of about 5 cm and the adhesives 830 may have a radius of about 3 cm. Thus, in some embodiments, a multi-laminar repair matrix may comprise patches 120, 140 that are pre-adhered pre-operatively. The pre-adhered multi-laminar repair matrix may be implanted to a tissue defect 110 such that the area of adhesion 1010 between the two patches 120, 140 is aligned with the tissue defect 110, and the tissue surrounding the tissue defect 110 is disposed in between the un-adhered peripheral regions 840 of the patches 120, 140. The separation distance between the und-adhered peripheral regions 840 of the two patches 120, 140, illustrated by the arrow 860 in FIG. 10, may be designed to approximate the thickness of a tissue surrounding a tissue defect 110. The patches 120, 140 may be connected to each other with the central regions 850 connected and the peripheral regions 840 unconnected according to any suitable mechanism known in the art.

In some embodiments, two patches 120, 140 may be separated by a smaller intermediate patch in between the two patches 120, 140. Thus, referring to FIG. 10*b*, in some embodiments, instead of adhesive 830, an intermediate patch can be located in its place. Thus, in some embodiments, a multi-laminar repair matrix 100 may include three layers of patches 120, 140. In some embodiments, the materials of the three layers of patches 120, 140 may be the same. In other embodiments, the materials of the three layers of patches 120, 140 may vary.

In some embodiments, the shape of the patches 120, 140 may vary from the standard square geometry shape wherein the patch 120, 140 is shaped as a square with equal length and width and constant thickness. In a multi-laminar repair matrix 100, the top patch 140 and/or bottom patch 120 may have a shape that varies from the standard square geometry shape. In a single-laminar repair matrix comprising only one patch 120, 140, which may be implanted to the inner surface or outer surface of a tissue defect 110, that single patch 120, 140 may also have a shape that varies from the standard square geometry shape. In addition, in embodiments where adhesives 220 are included on the patch 120, 140, the shape of the adhesive 220 may similarly vary. Many shapes are possible for the patch 120, 140 and/or adhesives 220. In some embodiments, the size of the patch 120, 140 and/or adhesives 220 may vary depending on its application and the size of the tissue defect 110.

Figure 11A:
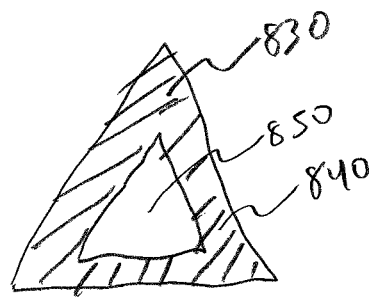
FIG. 11a illustrates a triangular patch with adhesives according to one embodiment.
Figure 11B:
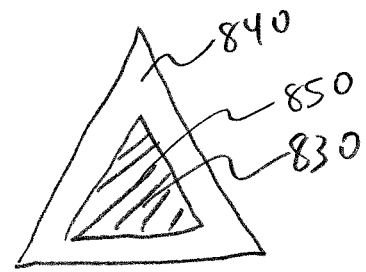
FIG. 11b illustrates a triangular patch with adhesives according to one embodiment.

For example, in some embodiments, the shape of the patches 140, 120 match the shape of a tissue defect 110. For example, the patches 120, 140 can have a shape that follows the perimeter of the tissue defect 110. For example, for procedures leaving a triangular shaped defect 110 in a tissue, the patches 120, 140 may be triangular, as illustrated in FIGS. 11*a-b*. Thus, the patch 120, 140 may define a triangle. In some embodiments, the length of the base of the triangular shaped patch 120, 140 may be between about 0.5 cm and 10 cm, the height of the triangular shaped patch 120, 140 may be between about 1 cm and 20 cm, and the angle at the vertices of the triangular shaped patch 120, 140 may be between about 5° to about 85°. In some embodiments, a triangular shaped patch 120, 140 may have a base of about 4 cm and a height of about 8 cm. Such a configuration may be optimized for surgical repair of defects in the posterior fossa, such as surgical repair of Chiari malformations. In these embodiments, the material of the patch 120, 140 may be designed with added thickness and mechanical strength to withstand increased biological pressure applied to the patch 120, 140 following surgical implantation.

Additionally, as illustrated in FIG. 11*a*, a hollow triangular shaped adhesive 830 may be included on the peripheral region 840 of the top 140 and/or bottom patch 120. Thus, the adhesive 830 may define a hollow triangle. Referring to FIG. 11b, the central region 850 of the top 140 and/or bottom patch 120 may also include a triangular shaped adhesive 830. Thus, the adhesive 830 may define a triangle.

In some embodiments, the patch 120, 140 may be circular and have a diameter of less than 1 cm to more than 10 cm. In some embodiments, the radius of a circular patch 120, 140 can be between about 0.5 cm and 10 cm. For example, a circular patch 120, 140 may have a radius of about 5 cm. Such a configuration may be optimized for repairing tissue defects in the cranium or calvarium, such as surgical excision of tumors or neoplasms. In these embodiments, the patch 120, 140 may be designed with reduced mechanical strength yet increased resistance to externally delivered radiation, increased sealing capabilities, and optimized cellular or tissue ingrowth following surgical implantation. In other embodiments, a circular patch 120, 140 may have a radius of about 0.5 cm. Such a configuration may be optimized for repair of tissue defects in and around the spine and spinal cord, which may occur during common spinal fusion or instrumentation procedures. In these embodiments, the material of the patch 120, 140 may be designed with increased mechanical strength and increased sealing capabilities.

In some embodiments, a circular patch 120, 140 with a radius of about 5 cm may also include a circular shaped adhesive 830 in the center of the patch 120, 140. The circular shape adhesive 830 may be 3 cm in some embodiments.

In some embodiments, the shape of the patch 120, 140 may be elliptical. For example, the long axis of the patch 120, 140 may be between about 1 cm and 20 cm, and the short axis may be between about 0.5 cm and 10 cm. In some embodiments, an elliptical patch may have a short axis of about 3 cm and a long axis of about 10 cm. Such a configuration may be optimized for surgical repair of defects in the posterial fossa, such as surgical repair of Chiari malformations. In these embodiments, the patch 120, 140 may be designed with added thickness and mechanical strength to withstand increased biological pressure applied to the patch 120, 140 following surgical implantation.

In some embodiments, the shape of the patch 120, 140 may be hexagonal. For example, a hexagonally shape patch may have a length and width between about 1 cm and 20 cm.

In some embodiments, the shape of the patch 120, 140 may be quadrilateral. For example, a quadrilateral patch 120, 140 may have a base between about 1 cm and 10 cm, and the height of the quadrilateral patch 120, 140 may be between about 0.5 cm and 10 cm.

In some embodiments, the patch 120, 140 may have a constant thickness. For example, the thickness of the patch 120, 140 may be between about 0.1 mm and 4 mm. In other embodiments, the patch 120, 140 may have a variable thickness. For example, the variable thickness may be designed according to the local mechanical and biological properties of the tissue defect 110.

In addition, adhesive 830 placed in a central region 850 of a patch 120, 140 may define a shape resembling that of the tissue defect 110. Further, adhesive 830 placed in a peripheral region 840 of a patch 120, 140 may define a hollow shape resembling that of the tissue defect 110. Thus, the patches 120, 140 and/or adhesives 830 may be square, rectangular, oval, etc. FIGS. 12a-b and 13a-b illustrate some exemplary shapes of patches 120, 140 with adhesive 830.

Figure 12A:
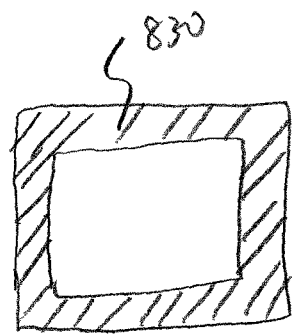
FIG. 12a illustrates a square patch with adhesives according to one embodiment.
Figure 12B:
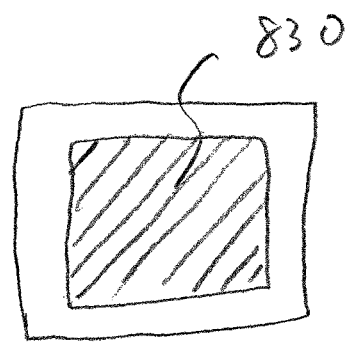
FIG. 12b illustrates a square patch with adhesives according to one embodiment.
Figure 13A:
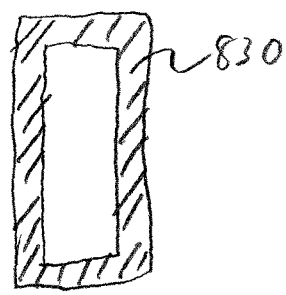
FIG. 13a illustrates a rectangular patch with adhesives according to one embodiment.
Figure 13B:
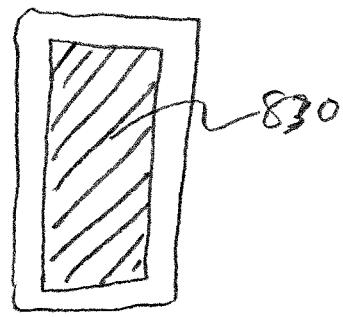
FIG. 13b illustrates a rectangular patch with adhesives according to one embodiment.

FIGS. 12a-b illustrate patches 120, 140 customized for repairing tissue defects 110 having a square shape. Specifically, the shape of the patches 120, 140 may be square. In addition, the patch 120, 140 may include adhesive 830 in the shape of a hollow square, as illustrated in FIG. 12 a. In another embodiment, the patch 120, 140 may include adhesive 830 in the shape of a square located at the center 850 of the patch 120, 140, as illustrated in FIG. 12b. FIGS. 13a-b illustrate patches customized for repairing tissue defects 110 having a rectangular shape.

In some embodiments, the shapes and sizes of the top 140 and bottom 120 patches may be different. In addition, the shapes and sizes of the adhesives 220 on the top 140 and bottom 120 patches may be different. For example, the bottom patch 120 may be a relatively large circular shaped patch 120 for plugging a tissue defect 110, and the top patch 120 may be a relatively smaller circular shaped patch 140 for suturing in to the tissue surrounding the tissue defect 110. Additionally, the patches 120, 140 may be customized in any number of different ways besides the shape and size. For example, the composition, mechanical properties, design, material, and fixation method can be specifically tailored for a certain tissue defect.

Accordingly, the multi-laminar repair matrix 100 and/or single laminar repair matrix and customized designs can provide superior outcomes post-operatively due to customization of the repair matrix to the tissue defect 110. In some embodiments, the repair matrix is pre-packaged and pre-customized by type of tissue defect 110. Thus, in some embodiments the repair matrix does not require significant shaping or customization for use in repairing a tissue defect 110. The pre-customized packages can improve the intra-operative efficiency of surgeons. Instead of hand-cutting patches in the operating room to fit a tissue defect 110, the surgeon can simply select the proper customized package for the appropriate tissue defect 110. In addition, the pre-customized repair matrix may have the benefits of more rapid deployment and implantation time, superior fit to the tissue defect 110, optimized mechanical properties pertaining to the tissue defect 110, and optimized biological properties pertaining to the tissue defect 110.

The adhesive 830 can promote faster healing time, improved quality repair of the tissue defect 110, and improved patient outcomes. Adhesive 830 between the tissue and patch 120, 140 can enhance the apposition and adhesion of the patch to the tissue, increase the strength of the seal, facilitate a water-tight seal, and encourage tissue ingrowth into the patch by promoting intimate contact with the tissue and cell sources/populations. Similarly, adhesive 830 securing a top patch 140 and a bottom patch 120 to each other over a tissue defect 110 can promote secure closure of the tissue defect 110, a complete seal of the peripheral tissue, and cellular infiltration leading to regeneration of native tissue. Additionally, adhesives 830 securing a patch 120, 140 to a tissue or adhesives 830 securing a patch 120, 140 to another patch 120, 140 through a tissue defect 110 can prevent migration of the patch and dehiscence.

The adhesives 830 can be made from any suitable materials, such as biologically derived adhesives (fibrin, fibronectin, collagen, etc.), synthetic adhesives (PEG/PEG hydrogels, acrylic solutions, cyanoacrylate solutions, 2-octyl cyanoacrylate, epoxy solutions, etc.) electrostatic/surface forces (electric charge, charge buildup, etc.), mechanical adhesion (fiber structure, entanglement, etc.). Further, the adhesives 830 can be formed onto the patch 120, 140 in any number of ways, such as chemical crosslinking, prolonged thermal processing, moderate mechanical entanglement, application of moderate adhesives, high-pressure physical lamination, or any other suitable method. In some embodiments, the material of the patch 120, 140 and/or the material of the adhesives 830 may include fibrin and/or cyanoacrylate. Fibrin and cyanoacrylate are generally known to have good adhesion properties for biological tissues. In addition, fibrin may be a natural structural element of native tissue, thus allowing cells to more rapidly bind onto the patch 120, 140 and/or adhesive 830 and migrate into the patch 120, 140.

In some embodiments, adhesives 830 are included on a patch 120, 140 that is compliant and conforms to the curvature of the tissue surrounding the defect 110. A compliant patch 120, 140 can increase the area of contact between the patch 120, 140 and the tissue. Thus, adhesives 830 may be placed anywhere throughout the patch 120, 140 and still adhere to tissue surrounding a defect 110 and/or to another patch 120, 140 through the tissue defect 110. In some embodiments, the bottom patch 120 and/or top patch 140 is compliant. Compliant patches 120, 140 can also increase handling, save time in the operating room, improve ease of use, and improve suturability.

The top patch 140 may be secured by adhesives only, sutures only, both adhesives and sutures, or any fixation technique known in the art. Thus, the top patch 140 may be secured by suturing, stapling, tacking, tucking, folding, pinning, crimping, sealing, tissue welding, gluing, fusing, adhesives, or any combination thereof. In some embodiments, the top patch 140 is implanted according to "onlay" techniques known in the art. The bottom patch 120 may be secured to the tissue defect 110 by adhesives 830 according to some embodiments of the invention. In some embodiments, the bottom patch 120 does not include adhesive 220, but the top patch 140 includes adhesive 830 for adhering to the bottom patch 120. Some embodiments provide for a multi-laminar repair matrix 100 without any adhesives 830, neither on the top patch 140 nor the bottom patch 120. External force exerted by fluid, such as cerebrospinal fluid in the dura mater, can help keep the bottom patch 120 in place and plug a tissue defect 110. Even without any adhesives 830, the multi-laminar repair matrix 100 achieves a high quality seal due to the additional layer of patch 120, 140 beneath the tissue defect 110.

In some embodiments, the adhesive elements 830 are used in a single-laminar patch system. For example, adhesives 830 may be included on the peripheral region 840 of a bottom patch 120 for adhering to the inner surface 130 of the peripheral tissue surrounding a tissue defect 110. In some embodiments, a top patch 140 is not implanted. In other embodiments, a top patch 140 is implanted to the outer surface of a tissue defect 110 but a bottom patch 120 is not implanted. The top patch 140 may include adhesive elements 830 for adhering to the outer surface of the tissue defect 110. The adhesives 830 and patch 120, 140 in a single laminar patch system may follow any number of different shapes, sizes, patterns, and configurations, as explained above with respect to the multi-laminar repair matrix 100.

Some embodiments include a single-laminar patch, such as a bottom patch 120, without any adhesives 830. External force exerted by fluid, such as cerebrospinal fluid in the dura mater, can help keep the bottom patch 120 in place and plug a tissue defect 110.

In some embodiments, the adhesive 830 may biodegrade and/or lose its adhesive properties after a certain amount of time. Some embodiments include a resorbable patch 120, 140 that biodegrade following implantation of the patch 120, 140 to a tissue defect 110. In some embodiments, the timing of resorbtion of the patch 120, 140 can be controlled. The adhesive 830 may last until the patch 120, 140 biodegrades or the adhesive 830 may last longer than the time it takes for the patch 120, 140 to biodegrade. For adhesives 830 adhering a patch 120, 140 to the peripheral tissue surrounding a tissue defect 110, the biodegrading time may be the same as the patch 120, 140 biodegrading time. For adhesives 830 adhering two patches 120, 140 together through a tissue defect 110, the biodegrading time may be longer than the patch 120, 140 biodegrading time. The adhesive 830 may also be designed to last until cells grow over the patch 120, 140, cells grow into the patch 120, 140, or the patch 120, 140 is integrated into the surrounding tissue. In some embodiments, the adhesive 830 biodegrading time is the same as, or longer than, the time it takes for substantial cell ingrowth into the patch 120, 140. A patch 120, 140 may include adhesives 830 with different biodegrading times on different regions of the patch 120, 140. In some embodiments, the biodegrade time of adhesive 830 on one patch (e.g. a bottom patch 120) is different than the biodegrading time of adhesive 830 on the other patch (e.g. a top patch 140). The biodegrade time of the adhesive 220 can range anywhere from less than a week to indefinitely (e.g. the adhesive 220 may not ever lose its adhesive qualities).

The adhesives 830 may further be utilized to adhere two patches 120, 140 together and thereby alter the strength of a patch 120, 140. For example, two patches 120, 140 adhered to each other via multiple restricting adhesion points provide rigidity and structure support. Further, different parts of a patch may be designed to exhibit different strengths. For example, two patches 120, 140 may be adhered to each other at the center of the patches 120, 140. Accordingly, the overall flexibility and compliance of the patches 120, 140 may be changed.

Figure 14A:
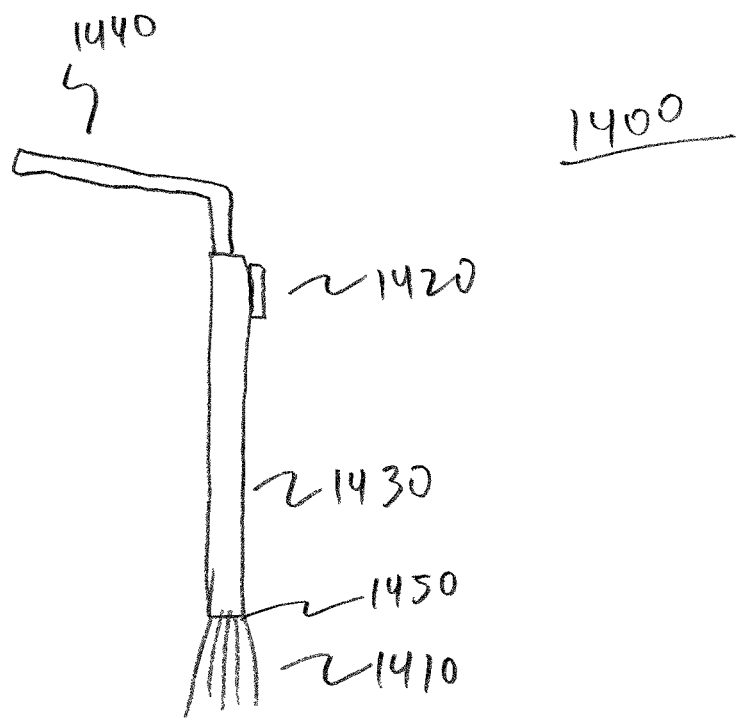
FIG. 14a illustrates a patch delivery system according to one embodiment.

The bottom 120 and/or top patch 140 may be deployed to a treatment site using the delivery system 1400 illustrated in FIG. 14*a*. FIG. 14*a* illustrates a patch delivery system ("PDS") 1400 with a shaft 1430, distal arms 1410, and a control 1420. The PDS 1400 may be made from plastic and/or surgical grade metal such as titanium alloy or nitinol. In some embodiments of the invention, the distal end of the shaft 1430 branches off into distal arms 1410 that are pivotally connected to the shaft 1430 at one or more connection points 1450. The distal arms 1410 provide a structural frame and support for holding a patch 120, 140 in a compressed state. The PDS 1400 may further include a control 1420 operably connected to the distal arms 1410. In some embodiments, the control 1420 is located toward the proximal end of the shaft 1430. Further, the length of the shaft 1430 may be variable. The distal arms 1410 may be made of nitinol, surgical grade stainless steel, or any other suitable material known in the art. In some embodiments, the distal arms 1410 may be thin so that they are flexible.

In some embodiments, the PDS 1400 includes a handle 1440 at the proximal end of the shaft 1430 for interoperative handling of the PDS 1400. The control 1420 may be placed at or near the handle 1440. The proximal end of the shaft 1430 may also include one or more Luer ports, check valve and similar components for infusion or aspiration of fluid and medicine. For example, the ports may allow the hydration of a patch prior to delivery. Such components are well known in the art.

The control 1420 may operate the distal arms 1410 by delivering a mechanical force or an electrical signal to the distal arms 1410. In some embodiments, the PDS 1400 is battery powered and/or wireless. The mechanical force may include a linear force, a torque, a stress, a strain, or other mechanical force. The mechanical force may be applied by a user's hand or robotic control and may be applied to the control 1420 on the PDS 1200. The electrical signal may include an electrical current, an electrical change in voltage, or other electrical signal. In some embodiments, the electrical signal controls the distal arms 1410 through a motor or other mechanism.

Figure 14B:
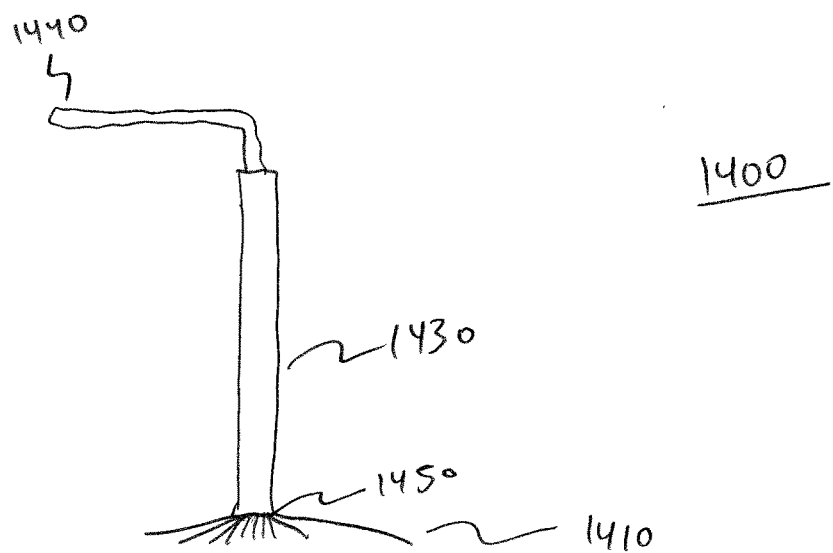
FIG. 14b illustrates a patch delivery system according to one embodiment.

Referring to FIG. 14*a*, the distal arms 1410 may be axially aligned with the axis of the shaft 1430 when the distal arms 1410 are in a first position. Referring to FIG. 14*b*, when the distal arms 1410 are in a second position, the distal arms 1410 may expand radially from the shaft 1430. Multiple other methods of arm deployment are possible. The distal arms 1410 may be extended from an axial position to a radial position by actuating the control 1420. The control 1420 may be a trigger, switch, button, knob or the like. The control 1420 may be configured to expand the distal arms 1410 radially in any number of ways. The control 1420 further includes a mechanism for returning the distal arms 1410 to an axial position, described herein as "releasing" the control 1420. The control 1420 may be released by moving a switch, knob, trigger, actuator, controller, etc. to another position. In another embodiment, the control 1420 includes two buttons, one for radially expanding the distal arms 1410 and one for compressing the distal arms 1410 to an axial position. The control 1420 may be released and actuated via any of the above and via any mechanism known in the art.

Figure 15A:
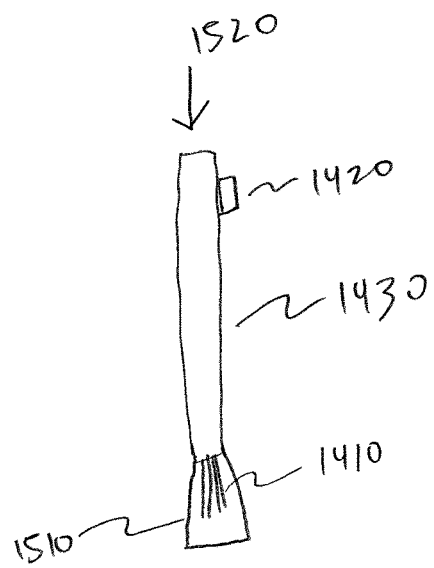
FIG. 15a illustrates a patch delivery system according to one embodiment.
Figure 15B:
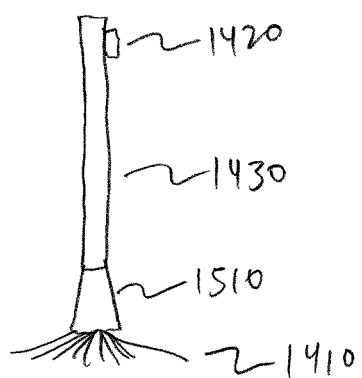
FIG. 15b illustrates a patch delivery system according to one embodiment.

Referring to FIG. 15*a*, in some embodiments, the distal arms 1410 are contained within a distal tube 1510 attached to the distal end of the shaft 1430. The distal arms 1410 may be contained in an axial position when inside the distal tube 1510 and biased radially so that when the distal arms 1410 are positioned outside the distal tube 1510, the distal arms 1410 expand radially, as illustrated in FIG. 15*b*. The distal arms 1410 may be positioned outside the distal tube 1510 by applying an axial distal force, as illustrated by the arrow 1520. Accordingly, in some embodiments, the control 1420 may be operably connected to the distal arms 1410 such that actuating the control 1420 applies an axial distal force, causing the distal arms 1410 to move axially and distally outside the distal tube 1510. The distal arms 1410 may be radially biased, such that the distal arms 1410 expand radially when moved outside the distal tube 1510. Further, releasing the control 1420 may cause the distal arms 1410 to retract proximally, back inside the distal tube 1510 and to an axial position.

Figure 16:
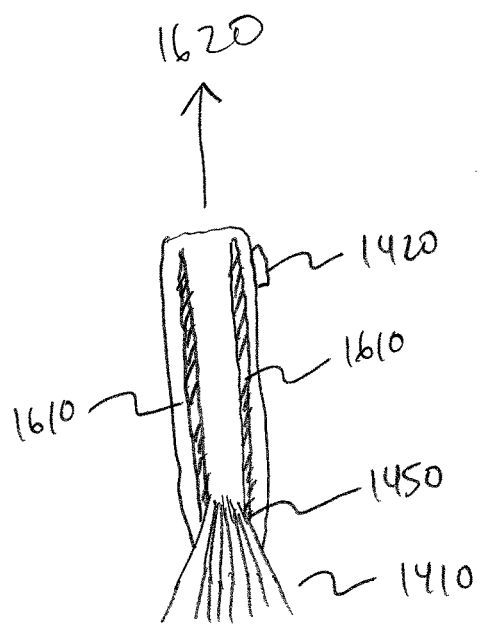
FIG. 16a illustrates a patch delivery system according to one embodiment.
FIG. 16b illustrates a patch delivery system according to one embodiment.
Figure 16:
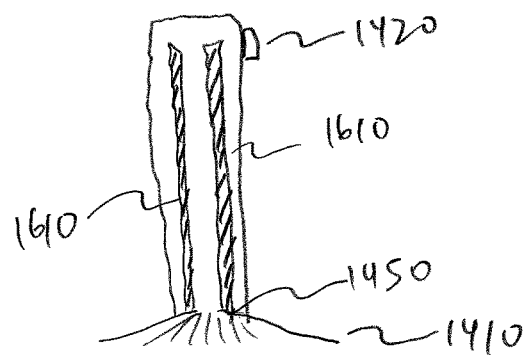

FIG. 16*a-b* illustrate another embodiment of radially expanding the distal arms 1210. Referring to FIG. 16*a*, a PDS 1400 may include linkages 1610 connected to the distal arms 1410 near the connection points 1450. Actuating the control 1420 can cause the linkages 1610 to move in the direction shown by the arrow 1620, thereby radially expanding the distal arms 1410.

In some embodiments, the patch 120, 140 may be parallel to the shaft 1430 when it is deployed to the tissue defect 110. The patch 120, 140 may be implanted flat on the tissue defect 110 by bending the shaft 1430, which can be flexible. In some embodiments, it may be advantageous for the patch 120, 140 to be parallel to the shaft 1430 due to the angle of insertion or approach to the tissue defect location (e.g. hernia).

Figure 17:
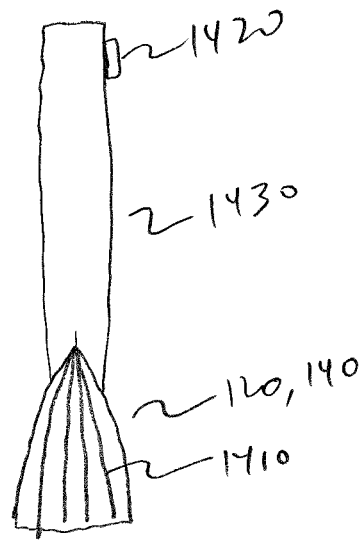
FIG. 17 illustrates a patch delivery system with a compressed patch loaded onto the patch delivery system according to one embodiment.
Figure 18:
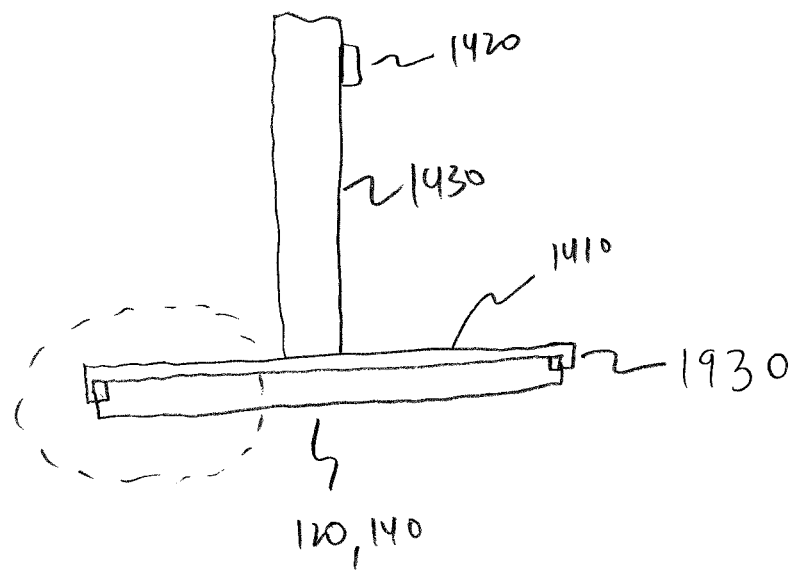
FIG. 18 illustrates a patch delivery system with a planar patch loaded onto the patch delivery system according to one embodiment.

FIG. 3 illustrates a compressed patch 120, 140 prepared for loading onto a PDS 1400. As illustrated in FIG. 3, in some embodiments, the patch 120, 140 in a compressed state can resemble the canopy of a closed umbrella. It will be appreciated that the patch 120, 140 may be compressed in a variety of other configurations as well. Referring to FIG. 3, in some embodiments, a compressed patch 120, 140 comprises a folded structure with one or more folding points. Thus, a compressed patch 120, 140 may define a peak 310, an outer surface 320, and an inner surface 330. In some embodiments, the peak 310 corresponds to the central region 850 of a patch 120, 140 when it is expanded to a substantially planar position. In some embodiments, the patch 120, 140 to be loaded onto a PDS 1400 can comprise multiple layers that have been pre-adhered to each other pre-operatively. For example, two patches 120, 140 may be adhered to each other via multiple restricting adhesion points to provide rigidity and structural support FIG. 17 illustrates a compressed patch 120, 140 loaded onto a PDS 1400 according to some embodiments of the invention. Referring to FIG. 17, the distal arms 1820 may be positioned over the outer surface 310 of a compressed patch 120, 140. FIG. 18 illustrates a PDS 1400 with distal arms 1410 that are radially expanded. In addition, FIG. 18 illustrates a patch 120, 140 in a substantially planar state attached to the radially expanded distal arms 1410. FIGS. 19*a-b*, 20*a-b*, and 21*a-b*, illustrate a close up view of the annotated portion of the PDS 1400 illustrated in FIG. 18. Referring to FIGS. 18, 19*a-b*, 20*a-b*, and 21*a-b*, in some embodiments, a PDS 1400 includes grips 1930 toward the distal end of the distal arms 1410. The grips 1930 may be clips, clamps, pincers, pinchers, grabbers, or the like, that secure the patch 120, 140 to the distal arms 1410 by holding the patch 120, 140 at the peripheral region of the patch 120, 140. The PDS 1400 may include a mechanism for controlling the release of the grips 1930. The mechanism may further allow control of how tightly the grips 1930 hold onto a patch 120, 140.

Figure 19A:
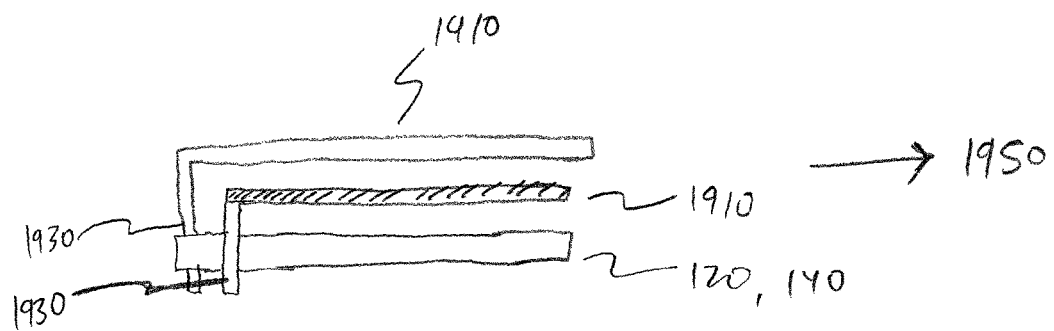
FIG. 19a illustrates a mechanism by which a patch delivery system holds and releases a patch according to one embodiment.
Figure 19B:
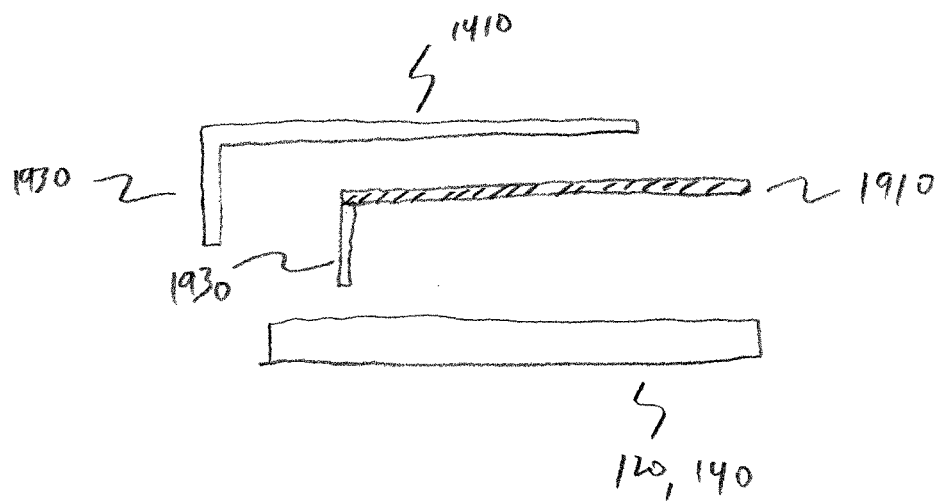
FIG. 19b illustrates a mechanism by which a patch delivery system holds and releases a patch according to one embodiment.

FIGS. 19*a-b*, 20*a-b*, and 21*a-b* illustrates various mechanisms by which the grips 1930 can hold and release a patch 120, 140. In some embodiments, a linkage 1910 can be coupled to a grip element 1930 through any suitable mechanism, such as mechanical or chemical. FIG. 19*a* illustrates two grip elements 1930, with a patch 120, 140 in between the grip elements 1930. As illustrated in FIG. 19*b*, moving one grip element 1930 relative to the other can increase the space between the grip elements 1930, thereby releasing the patch 120, 140. In some embodiments, a linkage 1912 coupled to a grip element 1930 can be utilized to release the patch 120, 140, by moving the linkage 1912 in the direction of the arrow 1950, as illustrated in FIG. 19*a*. In some embodiments, actuating the control 1420 on the PDS 1400 can move the linkage 1910 and thereby release the patch 120, 140.

Figure 20A:
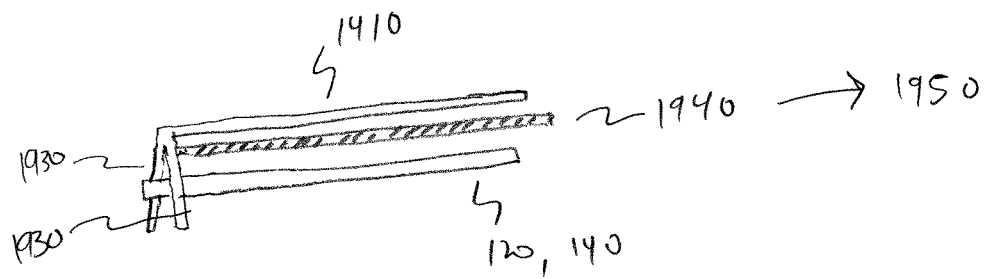
FIG. 20a illustrates a mechanism by which a patch delivery system holds and releases a patch according to one embodiment.
Figure 20B:
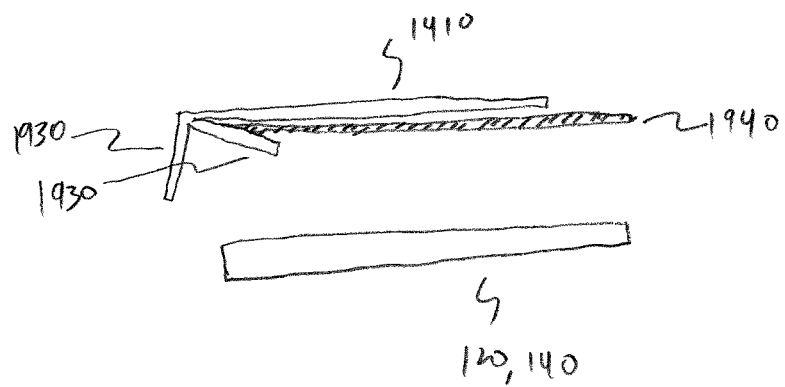
FIG. 20b illustrates a mechanism by which a patch delivery system holds and releases a patch according to one embodiment.

Referring to FIGS. 20*a-b*, two grip elements 1930 can be pivotally connected at the distal tip of a distal arm 1410. A linkage 1940 can be coupled to a grip element 1930. Referring to FIGS. 20*a-b*, moving the linkage 1940 in the direction of the arrow 1950 can increase the angle between the two grip elements 1930, thereby releasing the patch 120, 140.

Figure 21A:
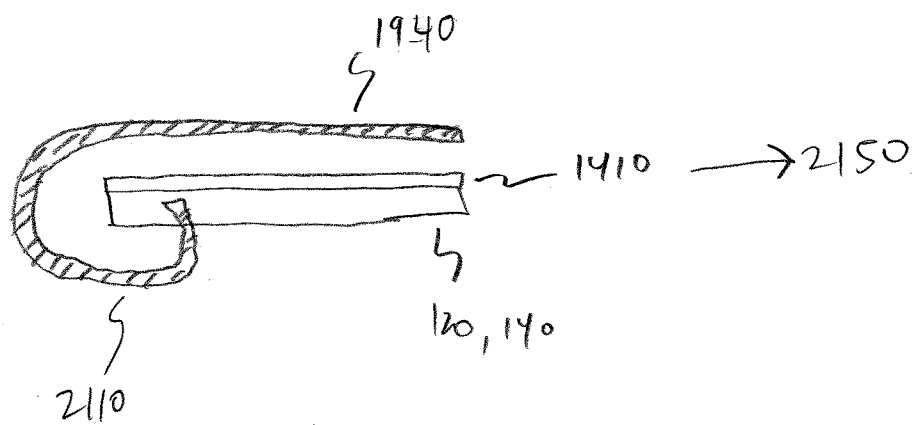
FIG. 21a illustrates a mechanism by which a patch delivery system holds and releases a patch according to one embodiment.
Figure 21B:
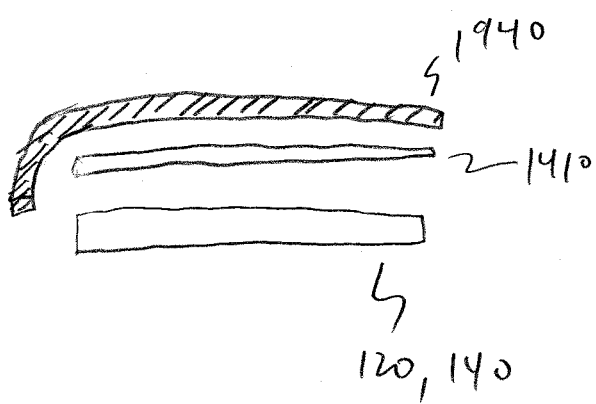
FIG. 21b illustrates a mechanism by which a patch delivery system holds and releases a patch according to one embodiment.

Referring to FIG. 21*a*, a linkage 1940 can extend past the distal arm 1410 and then curl underneath the patch 120, 140 and into the patch 120, 140 such that the tip of the linkage 1940 forms a coil 2110. The coil 2110 can be disposed so that it is inserted through the patch 120, 140 or partly through the patch 120, 140, thereby binding the distal arms 1410 and the patch 120, 140 together. Referring to FIGS. 21*a-b*, actuating the control 1420 on the PDS 1400 can cause the linkage 1940 to move in the direction of the arrow 2150, removing the coil 2110 from the patch 120, 140 and releasing the patch 120, 140 from the distal arms 1410.

Figure 22:
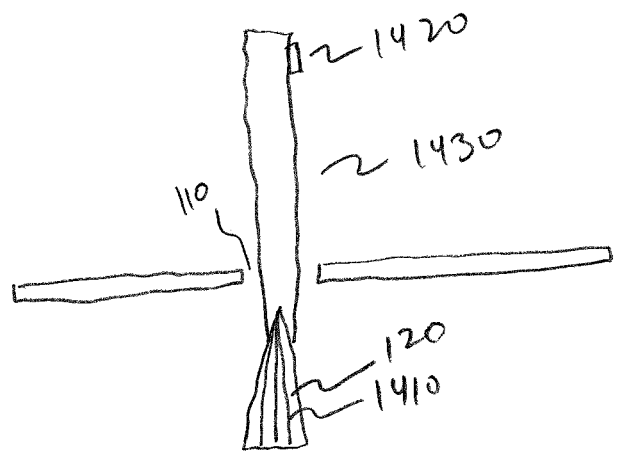
FIG. 22 illustrates a method of implanting a patch to a tissue defect using a patch delivery system according to one embodiment.
Figure 23:
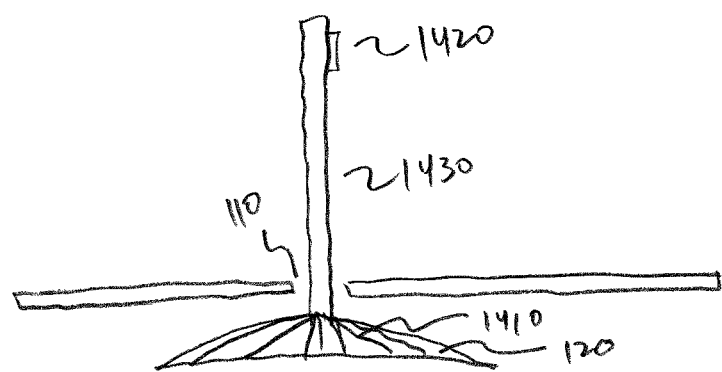
FIG. 23 illustrates a method of implanting a patch to a tissue defect using a patch delivery system according to one embodiment.
Figure 24:
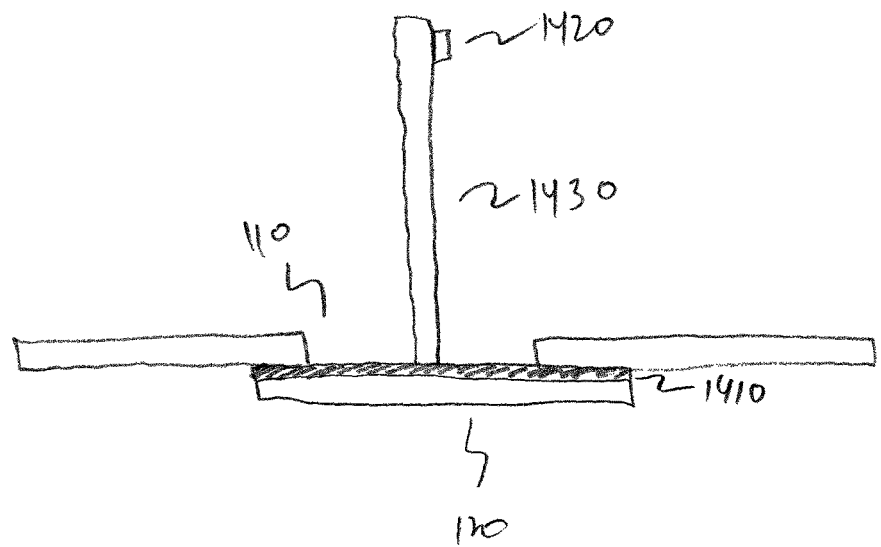
FIG. 24 illustrates a method of implanting a patch to a tissue defect using a patch delivery system according to one embodiment.

FIGS. 22-24 illustrate a PDS 1400 in use to deliver and implant a bottom patch 120 to the inner surface of a tissue defect 110, thereby plugging the tissue defect 110. Referring to FIG. 22, a PDS 1400 with a loaded bottom patch 120 is inserted through a tissue defect 110, until the entire length of the distal arms 1410 is distal (below) the tissue defect 110.

Referring to FIGS. 23-24, the control 1420 on the PDS 1400 may be actuated, causing the distal arms 1410 to expand radially, and thereby causing the bottom patch 120 to similarly expand, since the distal arms 1410 are attached to the bottom patch 120 via any of the mechanisms described above (e.g., grips 1930 that hold the patch 120). Accordingly, the bottom patch 120 may be expanded on the side distal to the tissue defect 110. The bottom patch 120 may be expanded from a compressed state to an expanded state that is substantially planar. The patch 120 may then be positioned laterally to ensure that the entire tissue defect 110 is plugged by the bottom patch 120. The patch 120 may also be moved in a proximal direction, bringing the patch 120 in contact with the inner surface 130 of the tissue defect 110.

After the expanded bottom patch 120 is brought to the desired position, the distal arms 1410 may be detached from the patch 120. For example, grips 1930 that were holding on to the patch 120 may be released. In addition, the control 1420 on the PDS 1200 may be released, causing the distal arms 1410 to return to an axial position and detach from the patch 120. In some embodiments, releasing the control 1420 also causes the distal arms 1410 to retract proximally, thereby detaching from the patch 120.

After the bottom patch 120 is implanted, a top patch 140 may also be implanted according to some embodiments of the invention. In some embodiments, only a bottom patch 120 is implanted, and no top patch 120 is implanted. In other embodiments, only a top patch 140 is implanted. A top patch 140 may be implanted to a tissue defect 110 in a similar manner as the bottom patch 120.

Figure 25:
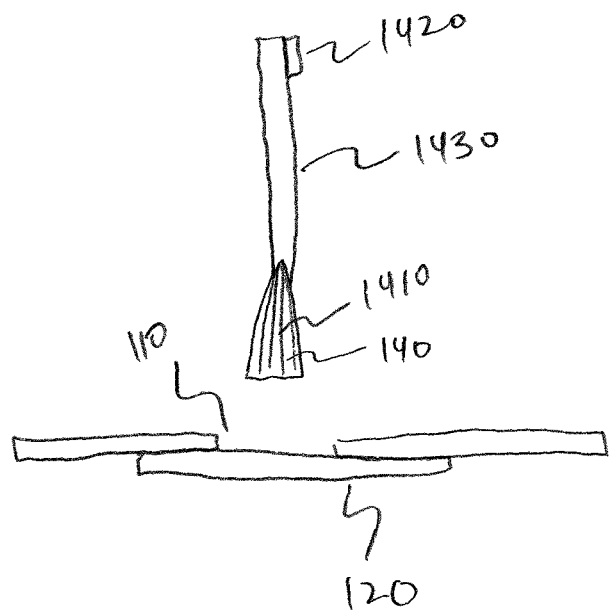
FIG. 25 illustrates a method of implanting a second patch to a tissue defect using a patch delivery system according to one embodiment.
Figure 26:
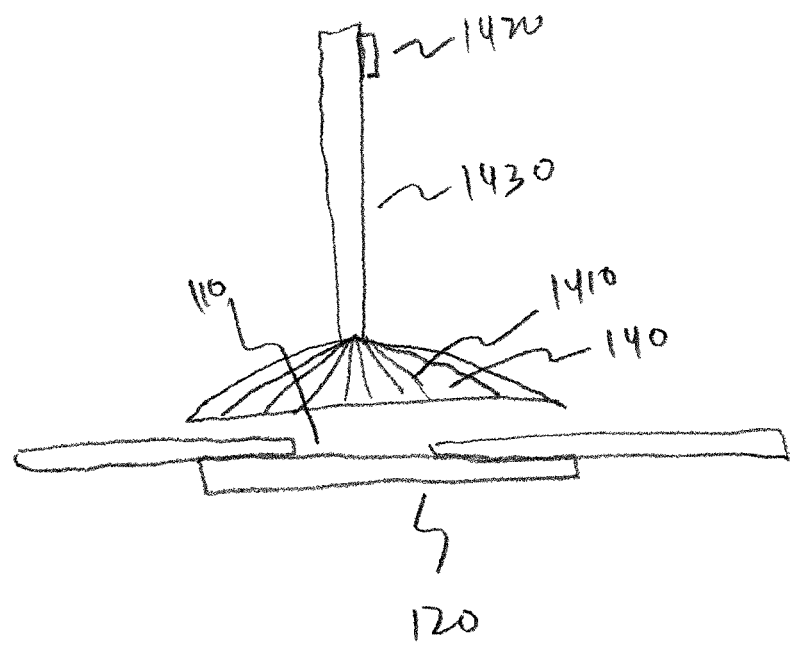
FIG. 26 illustrates a method of implanting a second patch to a tissue defect using a patch delivery system according to one embodiment.
Figure 27:
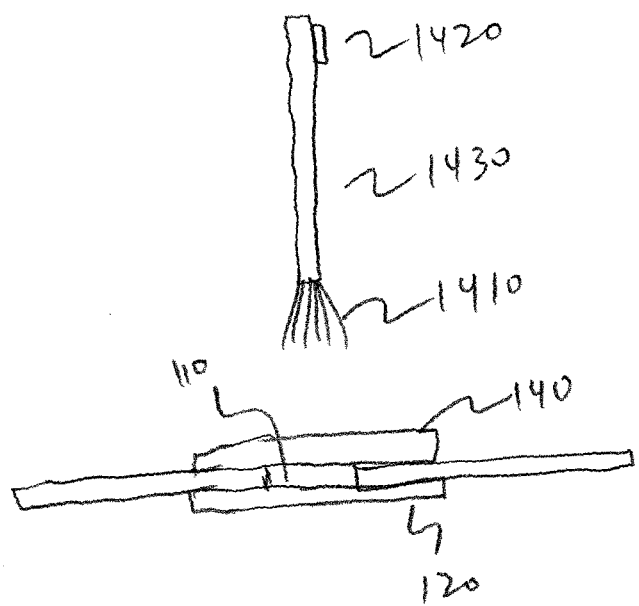
FIG. 27 illustrates a method of implanting a second patch to a tissue defect using a patch delivery system according to one embodiment.

FIGS. 25-27 illustrate a method of implanting a top patch 140 to a tissue defect 110. Although FIGS. 25-27 depict a bottom patch 120, it will be appreciated that the disclosed methods may also be used to implant a top patch 140 to a tissue defect 110 without a bottom patch 120.

Referring to FIG. 25, a PDS 1400 with a loaded compressed top patch 140 is positioned over a tissue defect 110. Referring to FIG. 26, a control 1420 on the PDS 1400 may be actuated, causing the distal arms 1410 to expand radially and the top patch 140 to similarly expand. Next, the PDS 1400 may be used to move the top patch 140 to a desired position. For example, the top patch 140 may be positioned to contact the outer surface of a tissue defect 110 and completely cover the tissue defect 110. Referring to FIG. 27, the control 1420 may be released, causing the distal arms 1410 to return to an axial position and detach from the top patch 140.

The PDS 1400 may be used with any number of types of patches 120, 140. For example, in some embodiments a compliant patch 120, 140 may be used with the PDS 1400. The compliant nature of the patch 120, 140 allows the patch 120, 140 to be compressed and held by the distal arms 1410. In some embodiments, the patch 120, 140 may comprise a dural substitute formed by electro-spinning methods, as described in PCT/US2011/040691, the entirety of which is hereby incorporated herein by reference. Thus, in some embodiments, a patch 120, 140 comprising electro-spun fibers may be used with the PDS 1400. Other examples of patches 120, 140 which may be used with the PDS 1200 include dural substitutes comprising resorbable polymer materials, non-resorbable polymeric materials, xenogenic collagen materials, processed collagen materials, processed allogenic tissue, nanofiber dural substitutes, multi-laminar nanofiber materials, patterned/reinforced nanofiber materials, synthetic (PGLA, PLGA, PCL, PC, PGA, PLA, PPY, PMMA, PEU, PU, etc.), Biologic (collagen, laminim, elastin, fibronectin, fibrin, SIS, dermis, dura, pericardium, fascia lata, etc.), electrospun material, woven materials, and processed human tissue (allograft, autograft, xenograft, etc.). In some embodiments, the thickness of the patch 120, 140 is between about 0.1 mm and 4 mm.

In some embodiments, the top patch 140 and/or bottom patch 120 contain shape memory, allowing the patch 120, 140 to return from a deformed state (e.g. compressed state) to its original shape (e.g. planar). Thus, although the distal arms 1410 on a PDS 1400 may help to expand the patch 120, 140, the distal arms 1410 may not be necessary for the patch 120, 140 to expand when the patch 120, 140 contains shape memory. Further, when the distal arms 1410 are used to expand a patch 120, 140 with shape memory, less force is required to radially expand the distal arms 1410 and cause the patch 120, 140 to expand.

Figure 28:
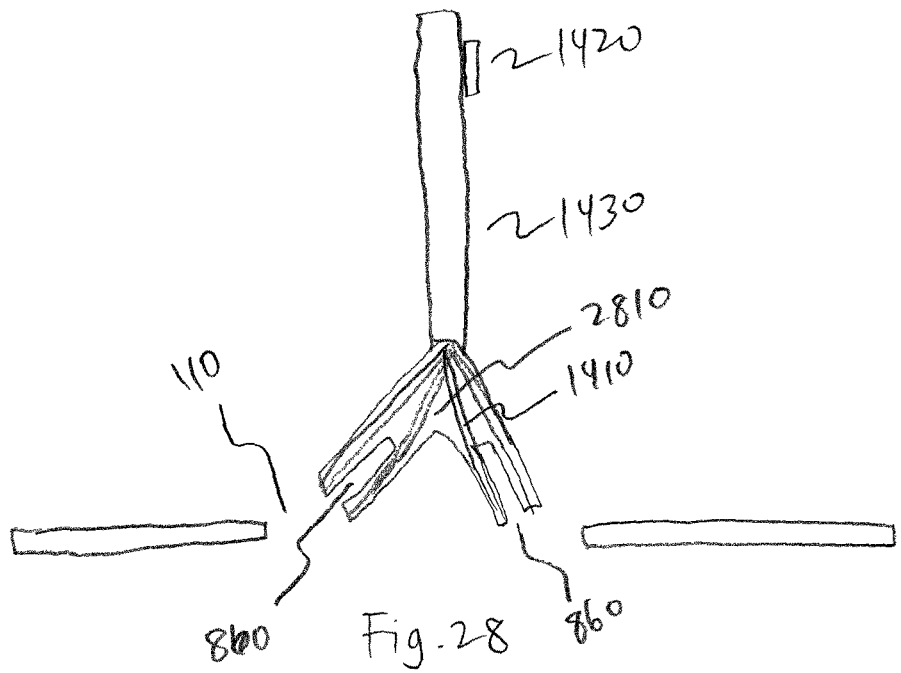
FIG. 28 illustrates a method of implanting a pre-adhered multi-laminar repair matrix to a tissue defect using a patch delivery system according to one embodiment.
Figure 29:
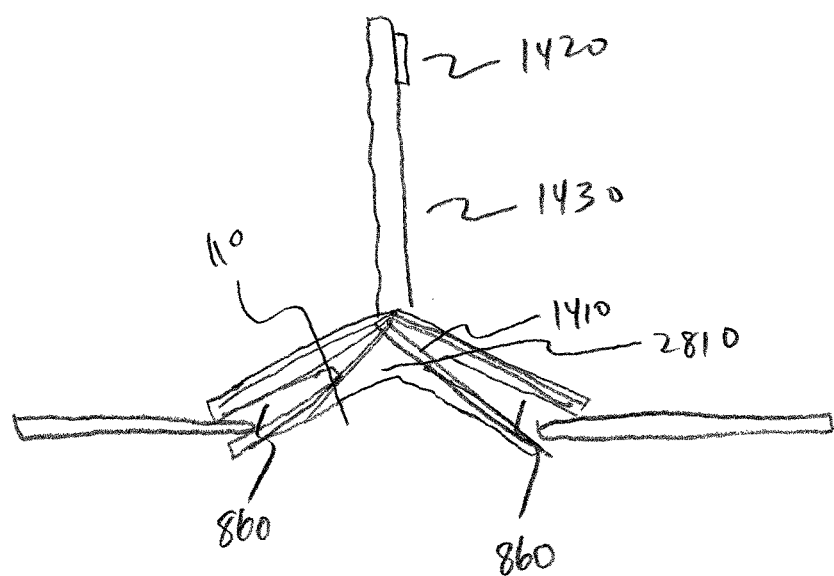
FIG. 29 illustrates a method of implanting a pre-adhered multi-laminar repair matrix to a tissue defect using a patch delivery system according to one embodiment.
Figure 30:
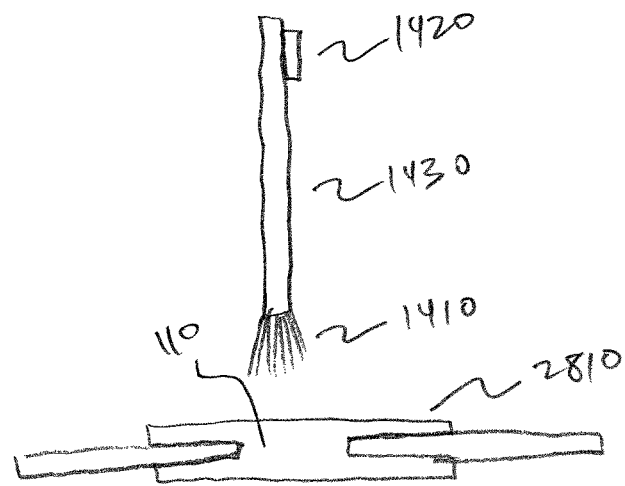
FIG. 30 illustrates a method of implanting a pre-adhered multi-laminar repair matrix to a tissue defect using a patch delivery system according to one embodiment.

FIGS. 28-30 illustrate a method of implanting a multi-laminar repair matrix that has been pre-adhered pre-operatively 2810, as described above with respect to FIG. 10. The pre-adhered multi-laminar repair matrix 2810 may comprise a top patch 140 and a bottom 120 adhered to each other at the central regions 850, and un-adhered at the peripheral regions 840, thus defining a slot 860 between the top 140 and bottom 120 patches. Referring to FIGS. 28-30, the pre-adhered multi-laminar repair matrix 2810 may be compressed and loaded onto the distal arms 1410, then expanded to a planar state by actuating the control 1420 on the PDS 1400. In some embodiments, the pre-adhered multi-laminar matrix 2810 may be implanted such that the slots 860 receive the tissue surrounding the tissue defect 110 at substantially the same time. In some embodiments, the top and bottom portions of the slot 860 are flexible.

In some embodiments, patches 120, 140 may be pre-loaded onto the distal arms 1210 of the shaft 1430 and further may be pre-customized by type of tissue defect 110. Accordingly, the shape of the patches 120, 140 and/or adhesive 830 may resemble the shape of a tissue defect 110. For example, the patches 120, 140 may have a shape that follows the perimeter of the tissue defect 110. Thus, a physician may select a PDS 1400 with a pre-loaded and pre-customized patch 120, 140 according to the type of tissue defect 110 that the physical will repair.

Figure 31A:
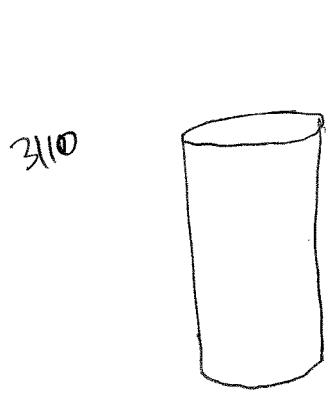
FIG. 31a illustrates a cartridge configured to attach to a patch delivery system according to one embodiment.
Figure 31B:
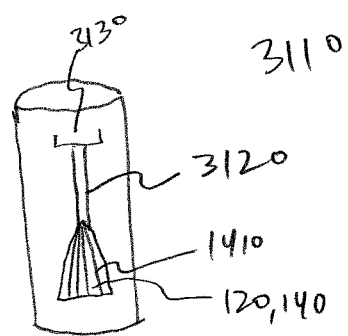
FIG. 31b illustrates the contents of the cartridge of FIG. 31a according to one embodiment.
Figure 32:
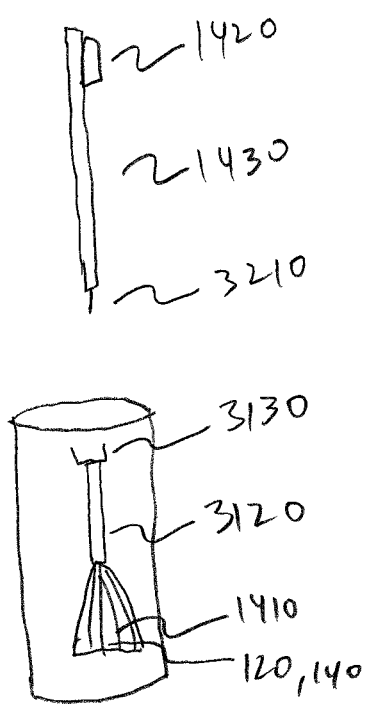
FIG. 32 illustrates a cartridge and patch delivery system detached from each other according to one embodiment.

FIG. 31a illustrates a pre-loaded cartridge 3110 according to some embodiments of the invention. FIG. 31b illustrates the contents of the pre-loaded cartridge 3110 according to some embodiments. In some embodiments, the distal arms 1410 are removably attached to the shaft 1430 of a PDS 1400. As illustrated in FIG. 31b, the pre-loaded cartridge 3110 may include a distal shaft 3120 and distal arms 1410 at the distal end of the distal shaft 3120. The distal shaft 3120 may be detached from the proximal shaft 1430, as illustrated in FIG. 32. Referring to FIG. 31b, the pre-loaded cartridge 3110 may also include a compressed patch 120, 140 loaded onto the distal arms 1410, and a linkage 3130 at the proximal end of the distal shaft 3120. In some embodiments, the distal arms 1410 does not include a pre-loaded compressed patch 120, 140. FIG. 32 illustrates one embodiment of a proximal shaft 1430 removed from the distal shaft 3120. Referring to FIG. 32, in some embodiments the proximal end of the distal shaft 3120 may include a linkage 3130. In addition, the distal end of the proximal shaft 1430 may include a linkage 3210. The pre-loaded cartridge 3110 may be connected to the distal end of the proximal shaft 1430 by connecting the linkage 3210 in the proximal shaft 1430 to the linkage 3130 in the distal shaft 312. The pre-loaded cartridge 3110 and the proximal shaft 1430 may also be connected according to any suitable mechanism known in the art. In some embodiments, the proximal shaft 1430 is re-usable and the pre-loaded cartridge 3110 and its components are disposable. The pre-loaded cartridge 3110 may come in a variety of configurations, including those for different types, shapes, and sizes of tissue defects 110.

In some embodiments, a kit may be provided and customized for certain tissue defects 110. The kit may advantageously include components such as a PDS 1400, reloadable cartridges 3110, a multi-laminar repair matrix 100, a single laminar repair matrix, saline, sutures, rulers, a gauze, any other surgical dressing, and the like. This kit may be contained in a sterile environment in containers well known in the art. For example, the containers may be plastic bags that are secured and easily opened. All the components inside the kit may be sterilized before being packaged in the container.

In some embodiments, the kit may include a reloadable cartridge 3110 and a PDS 1400 detached from the distal shaft 3120 and distal arms 1410. A patch 120, 140 may be pre-loaded onto the distal arms 1410 packaged in the reloadable cartridge 3110. In other embodiments, a patch 120, 140 may not be pre-loaded and may be separate from the distal arms 1410 packaged in the reloadable cartridge 3110. The patch 120, 140 may be sized and shaped to repair a certain tissue defect 110 of a similar size and shape. In addition, the kit may include a selection of several patches 120, 140 likely to work in the environment of a surgical procedure leaving a tissue defect 110 of a particular size and shape. For example, the kit may include a selection of several patches 120, 140 all having a triangular shape but having a different size in order to accommodate tissue defects 110 of varying sizes. The triangular shaped patches 120, 140 may be optimized for surgical repair of defects 110 in the posterior fossa, such as surgical repair of Chiari malformations. In addition, the triangular shaped patches may have a base with a length of about 0.5 cm and 10 cm, a height between about 1 cm and 20 cm, and angles at the vertices of the triangular shaped patch 120, 140 between about 5° to about 85°. As another example, the kit may include a selection of several patches 120, 140 having different shapes in order to accommodate tissue defects 110 of varying shapes. In some embodiments, the kit may include a PDS 1400 attached to the distal arms 1410. In other embodiments, the kit may include a reloadable cartridge 3110 and no PDS 1400. Any combination of components may be included in the kit. In some embodiments, the components are customized for certain tissue defects. For example, as explained above, the shape, size, and configuration of the patches 120, 140 and/or adhesives 830 may be customized.

In some embodiments, the PDS 1400 may be disposable after a single use. In other embodiments, the PDS 1400 may be re-usable. In some embodiments, the PDS 1400 is adapted to receive loadable cartridges containing patches.

Various modifications to the implementations described in this disclosure may be readily apparent to those skilled in the art, and the generic principles defined herein may be applied to other implementations without departing from the spirit or scope of this disclosure. Thus, the claims are not intended to be limited to the implementations shown herein, but are to be accorded the widest scope consistent with this disclosure, the principles and the novel features disclosed herein. Certain features that are described in this specification in the context of separate embodiments also can be implemented in combination in a single embodiment. Conversely, various features that are described in the context of a single embodiment also can be implemented in multiple embodiments separately or in any suitable subcombination. Moreover, although features may be described above as acting in certain combinations and even initially claimed as such, one or more features from a claimed combination can in some cases be excised from the combination, and the claimed combination may be directed to a subcombination or variation of a subcombination.

Similarly, while operations may be described as occurring in a particular order, this should not be understood as requiring that such operations be performed in the particular order described or in sequential order, or that all described operations be performed, to achieve desirable results. Further, other operations that are not disclosed can be incorporated in the processes that are described herein. For example, one or more additional operations can be performed before, after, simultaneously, or between any of the disclosed operations. In certain circumstances, multitasking and parallel processing may be advantageous. Additionally, other embodiments are within the scope of the following claims. In some cases, the actions recited in the claims can be performed in a different order and still achieve desirable results.

What is claimed is:

1. A repair matrix for repairing a tissue defect, comprising:
    a top flexible patch, the top flexible patch comprising a wholly synthetic dural substitute material that facilitates tissue growth, wherein a peripheral portion of the top flexible patch is configured to be implanted to an outer surface of tissue surrounding a tissue defect;
    a bottom flexible patch, the bottom flexible patch comprising material that facilitates tissue growth, wherein the bottom flexible patch in a first state is configured to be compressed and sized to facilitate implantation of a peripheral portion of the bottom flexible patch to an inner surface of the same tissue surrounding the tissue defect, and the bottom flexible patch in a second state is configured to be expanded such that the bottom flexible patch substantially conforms to a curvature of the tissue surrounding the tissue defect,
    wherein the bottom flexible patch in the first state comprises a distal end and a proximate end, wherein the distal end is configured to be inserted at least partially into the tissue defect before the proximate end,
    wherein the distal end of the bottom flexible patch in the first state corresponds to an outer perimeter of the bottom flexible patch in the second state, and wherein the proximate end of the bottom flexible patch in the first state corresponds to a portion of the bottom flexible patch spaced from the outer perimeter of the bottom flexible patch in the second state,
    wherein the bottom flexible patch in the second state comprises a top surface and a bottom surface, wherein the top surface faces the top flexible patch, wherein the top surface faces outward when the bottom flexible patch is in the first state, and wherein the bottom surface faces inward when the bottom flexible patch is in the first state,
    wherein a periphery of the top surface comprises an adhesive for adhering the top surface of the bottom flexible patch to the inner surface of the tissue surrounding the tissue defect, and
    wherein the bottom flexible patch comprises a plurality of creases, wherein the plurality of creases spans a diameter of the bottom flexible patch and intersects at the proximate end, wherein the plurality of creases are adapted to allow the bottom flexible patch to be substantially flattened when in the second state; and a connecting portion connecting a non-peripheral portion of the top flexible patch with a non-peripheral portion of the bottom flexible patch, the connecting portion comprising a height adapted to prevent adhesion of the bottom flexible patch to the top flexible patch, wherein the peripheral portion of the top flexible patch and the peripheral portion of the bottom flexible patch are separated by a void space, wherein the void space is sufficiently wide to allow the peripheral portion of the top flexible patch to be implanted to the outer surface of the tissue surrounding the tissue defect and the peripheral portion of the bottom flexible patch to be implanted to the inner surface of the same tissue surrounding the tissue defect, wherein the top flexible patch comprises a first biodegrade time, the bottom flexible patch comprises a second biodegrade time, and the adhesive comprises a third biodegrade time, wherein the third biodegrade time is longer than the first biodegrade time and the second biodegrade time.

2. The repair matrix of claim 1, wherein one or both of the top flexible patch and the bottom flexible patch comprises electro-spun fibers.

3. The repair matrix of claim 1, wherein the bottom flexible patch when in the second state has a shape that follows a perimeter of the tissue defect.

4. The repair matrix of claim 1, wherein a shape of the bottom flexible patch when in the second state is square, rectangular, circular, triangular, elliptical, hexagonal, or quadrilateral.

5. The repair matrix of claim 1, wherein one or both of the top flexible patch and the bottom flexible patch is configured to biodegrade after being implanted to the tissue surrounding the tissue defect.

6. The repair matrix of claim 1, wherein the tissue defect is a dural defect.

7. The repair matrix of claim 1, wherein the peripheral portion of the top flexible patch comprises an adhesive.

8. The repair matrix of claim 1, wherein a shape of the top flexible patch follows a perimeter of the tissue defect.

9. The repair matrix of claim 1, wherein a shape of the top flexible patch is square, rectangular, circular, triangular, elliptical, hexagonal, or quadrilateral.

10. The repair matrix of claim 1, wherein one or both of the top flexible patch and the bottom flexible patch comprises shape memory material.

11. The repair matrix of claim 1, wherein a width of the void space between the peripheral portion of the top flexible patch and the peripheral portion of the bottom flexible patch is adjustable to substantially match a width of the tissue surrounding the tissue defect.

12. The repair matrix of claim 1, wherein the connecting portion connecting the non-peripheral portion of the top flexible patch with the non-peripheral portion of the bottom flexible patch comprises an adhesive.

13. The repair matrix of claim 1, wherein the connecting portion connecting the non-peripheral portion of the top flexible patch with the non-peripheral portion of the bottom flexible patch comprises a material same as the material of the top flexible patch and/or the bottom flexible patch.

14. The repair matrix of claim 1, further comprising a delivery tool for implanting the bottom flexible patch to the inner surface of the tissue surrounding the tissue defect, wherein the delivery tool attaches to the proximate end of the bottom flexible patch in the first state to facilitate insertion of at least a part of the distal end of the bottom flexible patch in the first state into the tissue defect before the proximate end of the bottom flexible patch in the first state.

15. The repair matrix of claim 1, wherein the top flexible patch comprises a substantially similar size and a substantially similar shape as the bottom flexible patch.

16. A kit for repairing a dural defect, comprising:
a sterile easily opened packet containing a plurality of biodegradable patches configured to repair a dural defect for a range of expected patients undergoing a surgical procedure, wherein the plurality of biodegradable patches are of a same shape and varying sizes, such that at least one of the plurality of biodegradable patches comprises a size sufficiently large to cover the dural defect and enable a water-tight seal of the dural defect for one of the range of expected patients, wherein each of the plurality of biodegradable patches comprises a wholly synthetic dural substitute material, wherein each of the plurality of biodegradable patches comprises a plurality of creases, wherein the plurality of creases spans a diameter of each of the plurality of biodegradable patches and intersects at an internal point spaced from an outer perimeter on each of the plurality of biodegradable patches, wherein the plurality of creases are adapted to allow each of the plurality of biodegradable patches to be substantially flattened, wherein at least two or more of the plurality of biodegradable patches comprises a different biodegrade time wherein a periphery of a top surface of the at least two or more of the plurality of biodegradable patches comprises an adhesive for adhering the top surface of the flexible patch to the inner surface of the tissue surrounding the dural defect, and wherein the at least two or more of the plurality of biodegradable patches comprise a first biodegrade time, and the adhesive of the at least two or more of the plurality of biodegradable patches comprises a second biodegrade time, wherein the second biodegrade time is longer than the first biodegrade time.

17. The kit of claim 16, wherein the shape is square, rectangular, circular, triangular, elliptical, hexagonal, or quadrilateral.

18. The kit of claim 16, wherein each of the plurality of biodegradable patches comprises shape memory material.

19. A repair matrix for repairing a tissue defect, comprising:
a flexible patch, the flexible patch comprising a wholly synthetic dural substitute material formed by electro-spinning that facilitates tissue growth, wherein the flexible patch in a first state is configured to be compressed and sized to facilitate implantation of the flexible patch to an inner surface of tissue surrounding the tissue defect, and the flexible patch in a second state is configured to be expanded such that the flexible patch substantially conforms to a curvature of the tissue surrounding the tissue defect, wherein the flexible patch in the first state comprises a distal end and a proximate end, wherein the distal end is configured to be inserted at least partially into the tissue defect before the proximate end, wherein the distal end of the flexible patch in the first state corresponds to an outer perimeter of the flexible patch in the second state, and wherein the proximate end of the flexible patch in the first state corresponds to a portion of the flexible patch spaced from the outer perimeter of the flexible patch in the second state, wherein the flexible patch in the second state comprises a top surface and a bottom surface, wherein the top surface faces outward when the flexible patch is in the first state, and wherein the bottom surface faces inward when the flexible patch is in the first state, wherein a periphery of the top surface comprises an adhesive for adhering the top surface of the flexible patch to the inner surface of the tissue surrounding the tissue defect, wherein the flexible patch comprises a first biodegrade time, and the adhesive comprises a second biodegrade time, wherein the second biodegrade time is longer than the first biodegrade time, and wherein the flexible patch comprises a plurality of creases, wherein the plurality of creases spans a diameter of the flexible patch and intersects at the proximate end, wherein the plurality of creases are adapted to allow the flexible patch to be substantially flattened when in the second state.

20. The repair matrix of claim 19, further comprising a delivery tool for implanting the flexible patch to the inner surface of the tissue surrounding the tissue defect, wherein the delivery tool attaches to the proximate end of the flexible patch in the first state to facilitate insertion of at least a part of the distal end of the flexible patch in the first state into the tissue defect before the proximate end of the flexible patch in the first state.

* * * * *